US011406722B2

(12) United States Patent
Lux et al.

(10) Patent No.: US 11,406,722 B2
(45) Date of Patent: Aug. 9, 2022

(54) NANODROPLETS WITH IMPROVED PROPERTIES

(71) Applicant: The Board of Regents of The University of Texas System, Austin, TX (US)

(72) Inventors: Caroline de Gracia Lux, Austin, TX (US); Jacques Lux, Austin, TX (US); Alexander M. Vezeridis, Austin, TX (US); Robert F. Mattrey, Austin, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 0 days.

(21) Appl. No.: 15/923,845

(22) Filed: Mar. 16, 2018

(65) Prior Publication Data
US 2018/0272012 A1  Sep. 27, 2018

Related U.S. Application Data

(60) Provisional application No. 62/571,886, filed on Oct. 13, 2017, provisional application No. 62/472,524, filed on Mar. 16, 2017.

(51) Int. Cl.
*A61K 49/22* (2006.01)
(52) U.S. Cl.
CPC .......... *A61K 49/225* (2013.01); *A61K 49/226* (2013.01)
(58) Field of Classification Search
None
See application file for complete search history.

(56) References Cited

U.S. PATENT DOCUMENTS

| | | | |
|---|---|---|---|
| 5,558,853 A | 9/1996 | Quay | |
| 5,567,765 A | 10/1996 | Moore et al. | |
| 5,611,344 A | 3/1997 | Bernstein et al. | |
| 5,628,930 A * | 5/1997 | Weers ............... | A61P 7/08 516/56 |
| 5,730,955 A | 3/1998 | Lohrmann | |
| 5,798,091 A * | 8/1998 | Trevino ............... | A61K 49/227 424/9.52 |
| 6,113,919 A * | 9/2000 | Reiss ................ | A61K 9/0026 424/400 |
| 6,630,169 B1 | 10/2003 | Bot et al. | |
| 7,153,525 B1 | 12/2006 | Mumper et al. | |
| 2002/0150539 A1* | 10/2002 | Unger ................ | A61K 9/127 424/9.52 |
| 2009/0263329 A1* | 10/2009 | Wickline ............. | A61K 49/1896 424/9.37 |
| 2010/0105112 A1 | 4/2010 | Holtze et al. | |
| 2010/0267842 A1 | 10/2010 | Kiral et al. | |
| 2011/0110867 A1 | 5/2011 | Chung et al. | |
| 2013/0336891 A1* | 12/2013 | Dayton ............... | A61K 49/226 424/9.1 |
| 2014/0234223 A1 | 8/2014 | Port et al. | |
| 2015/0217246 A1 | 8/2015 | Holtze et al. | |

FOREIGN PATENT DOCUMENTS

| | | |
|---|---|---|
| EP | 2952212 A1 | 12/2015 |
| WO | 1999/053965 | 10/1999 |
| WO | 2013/045504 | 4/2013 |
| WO | 2015/147705 A1 | 10/2015 |
| WO | 2015/164756 A1 | 10/2015 |
| WO | 2015/164781 | 10/2015 |

OTHER PUBLICATIONS

Couture, O., et al., "Investigating Perfluorohexane Particles With High-Frequency Ultrasound" Ultra. Med. Biol., pp. 73-82 (Year: 2006).*
Porter, T., et al., "Targeted Transthoracic Acoustic Activation of Systemically Administered Nanodroplets to Detect Myocardial Perfusion Abnormalities", Circ. Card. Imag., pp. 1-7 (Year: 2015).*
Homogenizers.net, "High-Pressure Homogenization", accessed from: "https://homogenizers.net/pages/ac-high-pressure-homogenization" accessed on Nov. 20, 2021, pp. 1-2 (Year: 2021).*
Ren, W., et al., "A pressure-tolerant polymer microfluidic device fabricated by the simultaneous solidificationbonding method and flash chemistry application", Royal Society Chemistry, pp. 4263-4269 (Year: 2014).*
Bertilla, S.M., et al., "Semifluorinated Alkanes as Stabilizing Agents of Fluorocarbon Emulsions", Springer, pp. 237-251 (Year: 2005).*
Astafyeva, et al., "Perfluorocarbon Nanodroplets Stabilized by Fluorinated Surfactants: Characterization and Potentiality as Theranostic Agents," Journal of Materials Chemistry B 3(14):2892-2907 (2015).
Bertilla, et al., "Semifluorinated Alkanes as Stabilizing Agents of Fluorocarbon Emulsions," in: Artificial Oxygen Carrier, Keio University International Symposia for Life Sciences and Medicine 12:237-251 , Springer-Verlag, Tokyo © 2005.
Chattaraj, et al., "Selective Vaporization of Superheated Nanodroplets for Rapid, Sensitive, Acoustic Biosensing," Advanced Healthcare Materials 4(12):1790-1795 (2015).
Fang, et al., "A Study of the Formulation Design of Acoustically Active Liposheres as Carriers for Drug Delivery," European Journal of Pharmaceutics and Biopharmaceutics 67(1):67-75 (2007).

(Continued)

*Primary Examiner* — Michael G. Hartley
*Assistant Examiner* — Lance W Rider
(74) *Attorney, Agent, or Firm* — Womble Bond Dickinson (US) LLP

(57) ABSTRACT

Stable perfluorocarbon nanodroplet compositions with properties such as low-boiling points and small particle diameters are provided for improved performance in ultrasound imaging and therapeutic applications. Methods of producing stabilized nanodroplet compositions and methods of using the compositions are further provided to allow for improved performance in ultrasound imaging techniques and/or therapeutic applications.

19 Claims, 24 Drawing Sheets

(56) References Cited

OTHER PUBLICATIONS

Guedra, et al., "A Model for Acoustic Vaporization of Encapsulated Droplets," The Journal of the Acoustical Society of America 138(6):3656-3667 (2015).

Habif, et al., "Perfluorooctyl Bromide Dispersions in Aqueous Media for Biomedical Applications," Biotechnology Progress 8(5):454-457 (1992).

Ishijima, et al., "The Lifetime Evaluation of Vapourised Phase-change Nano-droplets," Ultrasonics 69:97-105 (2016).

Janjic, et al., "Perfluorocarbon Nanoemulsions With Fluorescent, Colloidal and Magnetic Properties," Biomaterials 35(18):4958-4968 (2014).

Kawabata, et al., "Nanoparticles With Multiple Perfluorocarbons for Controllable Ultrasonically Induced Phase Shifting," Japanese Journal of Applied Physics, 44(Part 1, No. 6B):4548-4552 (2005).

Kopechek, et al., "Cavitation-enhanced MR-guided Focused Ultrasound Ablation of Rabbit Tumors in Vivo Using Phase Shift Nanoemulstions," Physics in Medicine and Biology 59(13):3465-3481 (2014).

Kopechek, et al., "Synthesis of Phase-shift Nanoemulsions With Narrow Size Distributions for Acoustic Droplet Vaporization and Bubble-enhanced Ultrasound-mediated Ablation," Journal of Visualized Experiments 67:e4308 (2012).

Krafft and Riess, "Chemistry, Physical Chemistry, and Uses of Molecular Fluorocarbon-Hydrocarbon Diblocks, Triblocks, and Related Compounds—Unique 'Apolar' Components for Self-Assembled Colloid and Interface Engineering," Chemical Reviews 109(5):1714-1792 (2009).

Lattin, et al., "Formation of eLiposomes as a Drug Delivery Vehicle," Colloids and Surfaces, B: Biointerfaces 89:93-100 (2012).

Matsunaga, et al., "Phase-Change Nanoparticles Using Highly Volatile Perfluorocarbons: Toward a Platform for Extra Vascular Ultrasound Imaging," Theranostics 2(12):1185-1198 (2012).

Mountford, et al., "Condensation Phase Diagrams for Lipid-coated Perfluorobutane Microbubbles," Langmuir 30 (21):6209-6218 (2014).

Parlato, et al., "Synthesis, Characterization, and Applications of Hemifluorinated Dibranched Amphiphiles," The Journal of Organic Chemistry 76(16):6584-6591 (2011).

Porter, et al., "Targeted Transthoracic Acoustic Activation of Systemically Administered Nanodroplets to Detect Myocardial Perfusion Abnormalities," Circulation—Cardiovascular Imaging 9(1):ed003770 (2016).

Sheeran, et al., "Contrast-enhanced Ultrasound Imaging and in Vivo Circulatory Kinetics With Low-boiling-point Nanoscale Phase-change Perfluorocarbon Agents," Ultrasound in Medicine & Biology 41(3):814-831 (2015).

Sheeran, et al., "Decafluorobutane as a Phase-change Contrast Agent for Low-energy Extra Vascular Ultrasonic Imaging," Ultrasound in Medicine and Biology 37(9):1518-1530 (2011).

Shiraishi, et al., "A Facile Preparation Method of a PFC-containing Nano-sized Emulsion for Theranostics of Solid Tumors," International Journal of Pharmaceutics 421(2):379-387 (2011).

Williams, et al., "Characterization of Submicron Phase-Change Perfluorocarbon Droplets for Extravascular Ultrasound Imaging of Cancer," Ultrasound in Medicine and Biology 39(3):475-489 (2013).

Xu, "Multifunctional Microbubbles and Nanobubbles for Photoacoustic Imaging,"Contrast Media & Molecular Imaging 6(5):401-411 (2011).

\* cited by examiner

A

B

C

A

B form microbubbles when exposed to ultrasound stimulus at 8 MHz with a mechanical index (MI) of at least 0.4 for DFB or at least 0.16 for OFP nanodroplets.

NANODROPLETS WITH IMPROVED PROPERTIES

REFERENCE TO RELATED APPLICATIONS

This application claims the benefit of U.S. Provisional Application No. 62/472,524, filed Mar. 16, 2017, and U.S. Provisional Application No. 62/571,886, filed Oct. 13, 2017, each of which is herein incorporated by reference in its entirety.

STATEMENT REGARDING FEDERALLY SPONSORED RESEARCH

This invention was made with partial government support by funding from the Cancer Prevention and Research Institute of Texas under grant number RR150010. The government has certain rights in the invention.

STATEMENT REGARDING FEDERALLY SPONSORED RESEARCH

This invention was made with partial government support by funding from the Cancer Prevention and Research Institute of Texas under grant number RR150010. The government has certain rights in the invention.

FIELD OF THE INVENTION

The present invention relates to the field of medical diagnostics and therapeutics, and more specifically to the development of stabilized nanodroplets (NDs) for ultrasound (US) imaging or therapeutic use.

BACKGROUND OF THE INVENTION

Contrast-enhanced ultrasound (CEUS) imaging provides advantages over conventional ultrasound techniques by increasing image contrast and improving diagnostic accuracy. Existing strategies for contrast-enhanced ultrasound imaging are based on intravenous injection or the introduction of microbubbles into tissue to achieve increased contrast. Recent investigations have focused on the development, of phase-change contrast agents (PCCAs), including liquid perfluorocarbon nanodroplets that can be activated by an ultrasonic pulse to form microbubbles in vivo to enhance contrast. However, the use of PCCAs has been severely limited by the large particle size of existing nanodroplets and their spontaneous vaporization into microbubbles in the case of low-boiling point fluorocarbon nanodroplets, as well as unfavorable increases in liquid perfluorocarbon nanodroplet boiling points as particle size is decreased. A need, therefore exists for low-boiling point nanodroplets that exhibit small particle size and improved stability in vivo.

SUMMARY OF THE INVENTION

In one aspect, the invention provides stabilized nanodroplet compositions comprising a perfluorocarbon (PFC), a surfactant, and a co-surfactant, wherein the nanodroplet compositions have an average particle diameter of less than 300 nm. In certain embodiments, the PFC has a boiling point of less than about 0° C. In some embodiments, the PFC is decafluorobutane (DFB) or octafluoropropane (OFP)). The co-surfactant may comprise a semifluorinated alkane, such as an FnHm diblock, a linear semifluorinated alkane with the chemical formula $C_nF_{2n+1}C_mH_{2m+1}$. In further embodiments, the composition comprises an average particle diameter of less than about 250 nm, for example less than about 200 nm or less than about 150 nm. Other embodiments of the invention provide compositions wherein at least 90% of the nanodroplets in said composition have a particle size of less than about 300 nm, for example compositions having at least 90% of the nanodroplets in said composition have a particle size of less than about 200 nm. In certain embodiments, the composition is substantially free of microbubbles. In other embodiments, the composition has a nanodroplet concentration of at least $10^{11}$ NDs/mL, for example at least $10^{12}$ NDs/mL. In further embodiments the composition exhibits less than a 10% change in average particle diameter over a period of 1 week at 4° C., and in yet further embodiments the composition exhibits less than a 10% change in average particle diameter over a period of 1 hour at 37° C. The invention further provides embodiments in which the stabilized nanodroplet composition undergoes a phase change to form microbubbles when exposed to ultrasound stimulus at 8 MHz with a mechanical index (MI) of at least 0.4 for DFB or at least 0.16 for OFP nanodroplets.

In another aspect, the invention provides methods of enhancing contrast in ultrasound imaging, comprising the steps of: (a) providing a ND composition of the invention to a tissue; and (b) exposing said composition to an ultrasound stimulus at 8 MHz with a MI of at least 0.4 for DEB nanodroplets or at least 0.1.6 for OFP nanodroplets.

In yet another aspect, the invention provides methods of producing a nanodroplet, comprising the step of: emulsifying a PFC with surfactant and co-surfactant to form a nanodroplet composition having an average particle diameter of less than 300 nm. In some embodiments, the PFC has a boiling point of less than about 0° C. In other embodiments, the co-surfactant comprises a semifluorinated alkane. The invention further provides methods wherein emulsifying is carried out at less than about −15° C. for DFB nanodroplets or −35° C. for OFP nanodroplets, or wherein emulsifying is carried out at a pressure between about 2,000 psi and 13,000 psi. Nanodroplet compositions produced by the methods disclosed herein are further provided.

DETAILED DESCRIPTION

Figure 1A:
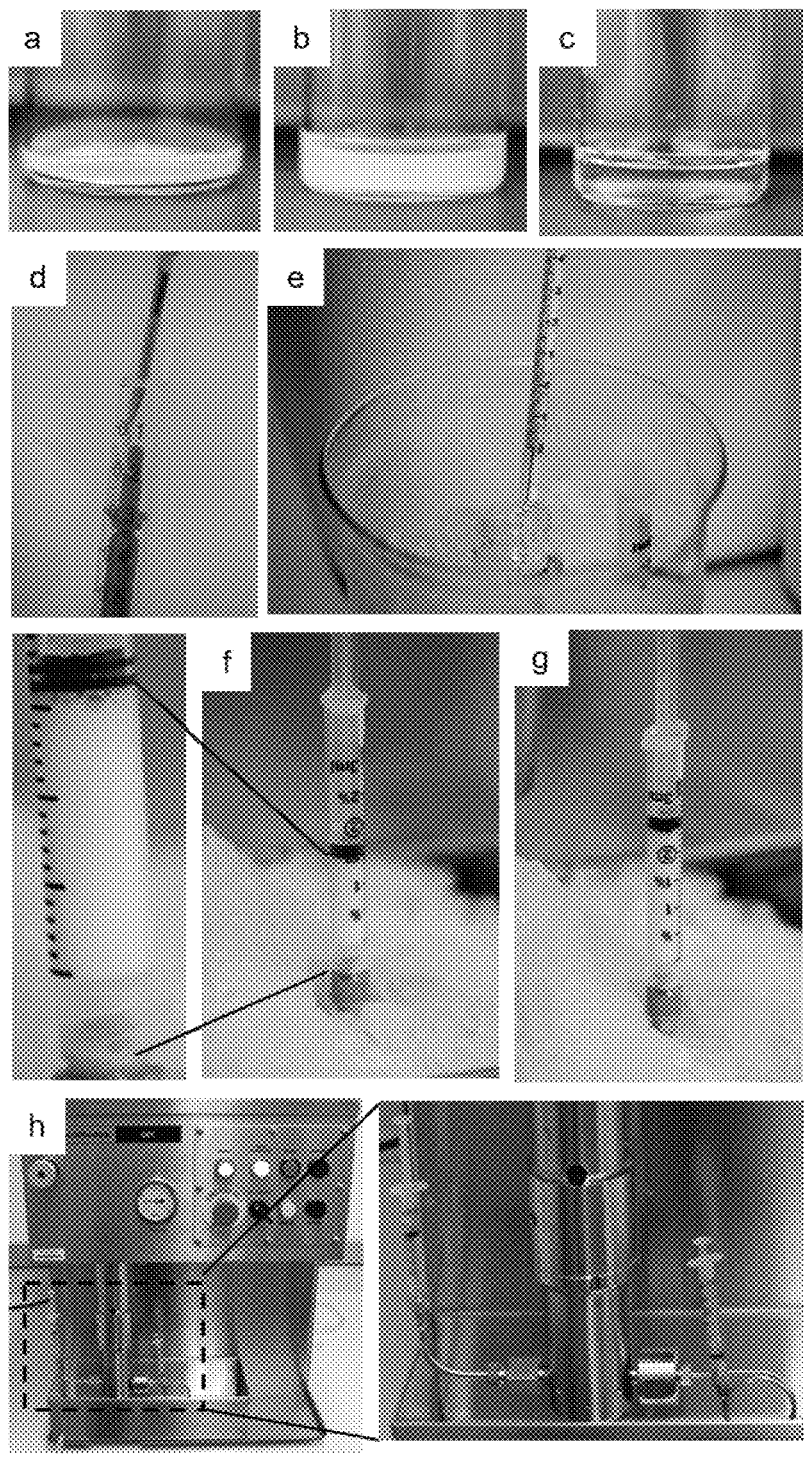
FIG. 1A shows an illustrative representation of exemplary DFB ND production steps: (panel a) representative picture of dry film composed of DSPC and DSPE-PEG2000 or DSPC, DSPE-PEG2000 and FnHm, (panel b) dry film dispersion in 2 mL of phosphate-buffered saline (PBS)/propylene glycol/glycerol in a 16:3:1 v/v/v ratio, (panel c) clear solution post sonication at 68° C., (panel d) liquid DEB in the syringe kept on dry ice, (panel e) sample cooling down for 2 min in a minus 20° C. ice/sodium chloride bath, (panel f) first pass through the LV1, (panel g) ninth pass, (panel h) Low Volume Microfluidizer (LV1, Microfluidics) with both coil, tray and 3 mL syringes.

Phase-change contrast agents (PCCAs) such as superheated perfluorocarbon (PFC) nanodroplets (NDs) are useful in the field of contrast-enhanced ultrasound (CEUS) imaging and ultrasound guided therapy. However, existing strategies for producing PCCAs of superheated PFCs rely on the production of microbubbles (MBs), followed by condensation to form NDs. This approach results in condensed ND compositions with polydisperse distributions further comprising high concentrations of larger MBs. Due to polydispersity, NDs produced by MB condensation methods have an unpredictable boiling point, limiting the utility of these NDs as PCCAs in imaging and therapeutic applications. A need therefore exists for stabilized low-boiling point ND compositions with a low mean ND diameter. In particular, NDs having a diameter of less than or equal to 500 nm, in particular less than about 300 nm, are needed for ultrasound imaging applications.

The invention therefore provides novel methods to achieve stabilized ND compositions comprising very low-boiling point PFCs near or below 0-degree C. that have a narrow size distribution and high concentration of NDs. The DFB NDs provided, by the invention are stable at physiological temperatures and are acoustically activated to form MBs when ultrasound pressure exceeds 0.4 mechanical index units (MI) at 8 MHz. The OFP NDs also provided by the invention are stable at physiological temperatures and are acoustically activated to form MBs when ultrasound pressure exceeds 0.15 MI at 8 MHz. In certain embodiments, the invention provides DEB NDs having an average diameter of less than or equal to about 300 nm. In certain embodiments, the invention provides OFP NDs having an average diameter of less than or equal to about 200 nm. The invention further provides methods of producing the stabilized NDs disclosed herein.

II. Stabilized Nanodroplets

The present invention provides methods to achieve stabilized ND compositions exhibiting improved properties for diagnostic and therapeutic ultrasound applications. In some embodiments, stabilized NI) compositions of the present invention comprise a PFC emulsified with a surfactant and co-surfactant to provide concentrated, monodisperse ND compositions having a small average particle size and low boiling point. ND compositions of the present invention are monodisperse, and comprise high concentrations of low-boiling point NDs having a small particle size. The invention further provides methods of preparing the disclosed stabilized ND compositions in a highly reproducible manner, and preventing the phenomenon of irreversible droplet-to-bubble transition, which is difficult to control at physiological temperature.

In some embodiments, the stabilized ND compositions of the invention exhibit a monodisperse distribution and are substantially free of MBs compared to conventional PCCA compositions. In certain embodiments, "substantially free of microbubbles" or "substantially free of MBs" refers to emulsion with no detectable MBs having a diameter above 500 nm as detected by TRPS, or no detection of NDs with diameter above 800 nm as detected by DLS. In further embodiments, the invention provides emulsions with no residual MBs present in the emulsions. As used herein, "monodisperse" refers to an ND composition wherein at least about 90% of the particles have diameters of less than about 300 nm and a polydispersity index (PDI) <0.2, as assessed by DLS. Further embodiments of the invention provide monodisperse DFB ND compositions wherein at least about 95%, for example at least about 96%, at least about 97%, at least about 98%, at least about 99%, or 100% of particles have diameters less than about 300 nm. Further embodiments of the invention provide monodisperse OFP ND compositions wherein at least about 95%, for example at least about 96%, at least about 97%, at least about 98%, at least about 99%, or 100% of particles have diameters less than about 200 nm. As used herein, "small" or a "small-diameter nanodroplet" or "small-diameter" refers to an ND having a smaller initial size or smaller initial diameter in the liquid state than a corresponding ND composition comprising the same components, but lacking a co-surfactant. By providing a large particle count and optimal distribution throughout the vascular space, the stabilized NDs of the present invention exhibit superior targeting of intravascular targets compared to larger NDs or MBs and are capable of targeting extravascular sites more efficiently than existing ND manufacturing technology by virtue of a smaller diameter and enhanced stability.

The methods of the present invention further provide stabilized ND compositions having a concentration of NDs of at least $10^{12}$ NDs/mL or greater. The stabilized ND compositions provided by the present invention may comprise NDs in much higher concentrations compared with conventional MB compositions that typically comprise approximately $10^9$ MBs/mL. In certain embodiments, the stabilized ND compositions of the present invention comprise at least about $10^{11}$ NDs/mL for example at least $10^{12}$ NDs/mL.

The stabilized ND compositions provided by the invention further exhibit stability over greater periods of time and at higher temperatures than corresponding ND compositions lacking a co-surfactant. In certain embodiments, the stabilized ND compositions provided by the invention exhibit no significant changes in size or derived count rate over a period of one week, two weeks, three weeks, one month, or more, when stored at a low temperature, for example a temperature about 4° C. or about −20° C. As used herein, "no significant change in size" refers to a change of less than 10%, for example less than 5%, or less than 1% in average particle diameter.

In further embodiments, the stabilized ND compositions of the present invention do not exhibit significant dissociation of NDs at temperatures of up to about 45° C., for example temperatures of up to 40° C. As used herein "significant dissociation" refers to the vaporization of at least 1%, for example at least about 2%, or at least about 5% of NDs to form MBs. In contrast, non-stabilized ND compositions lacking a co-surfactant exhibit significant dissociation of NDs above 40° C.

As used herein, "stable" or "stabilized nanodroplet" or "stable nanodroplet" refers to a nanodroplet having a longer circulation time in vivo than a corresponding ND composition comprising the same components, but lacking a co-surfactant. NDs obtained by the method disclosed herein will present higher vaporization signals compared to NDs obtained with the condensation method at the same concentration, as the majority of small particles present in the ND sample from the condensed method are non-echogenic liposomes and not NDs. The invention further provides stabilized nanodroplets prepared using the direct emulsification method provided herein that exhibit improved, properties compared to NDs prepared according to previously used methods, including improved concentration and monodispersity (absence of residual MBs and liposomes post-formulation).

The invention further provides stabilized ND compositions wherein the NDs are stable under in vivo conditions until activated by ultrasound stimulus. In certain examples, the DFB ND compositions of the present invention undergo a phase change in response to an ultrasound pressure of at least 0.4 MI at 8 MHz, for example under a pressure of 0.5 MI at 8 MHz. In further examples, the OFP ND compositions of the present invention undergo a phase change in response to an ultrasound pressure of at least 0.15 MI at 8 MHz. In specific embodiments, the stabilized NI) compositions of the invention are stable in the absence of ultrasound stimulus up to at least 37° C., but could begin to phase transition without ultrasound at approximately 45° C.

In certain embodiments, the invention provides NDs with reduced and narrow vaporization thresholds combined with a thermal stability above physiological temperature. The formulation and emulsification techniques provided herein result in several unique properties, including: 1) sub-300 nm NDs with narrow size distribution (PDI <0.2); 2) an absence of residual MBs; 3) high particle count (>10$^{12}$ NDs/mL); 4) high stability over days of storage at room temperature; 5) high stability over weeks of storage at 4° C.; and 6) stability at 37° C. and above without spontaneous phase transition of NDs to MBs until exposed to ultrasound at clinically relevant power (≥0.4 MI for DFB or ≥0.15 for OFP NDs). When the NDs of the invention phase transition to MBs they produce a high contrast-to-noise ratio using standard B-mode imaging at diagnostic MI. In addition, the NDs of the invention are longer lived than previously reported formulations, exhibiting stability over weeks to months when refrigerated.

In further embodiments of the invention, the addition of amphiphilic diblock F8H18 co-surfactants has been shown to stabilize NDs and make them more resilient to US exposure. Without wishing to be bound by theory, this enhanced stability is not only due to the production of smaller droplets that are more stable than larger ones but also results from the Dowell effect. The enhanced stability obtained at 37° C. may be associated with the disordering of the H18 blocks, which leads to better interdigitation of the F8H18 chains with the lipidic tails of the phospholipids constituting the shell of the ND.

The inventors have therefore shown that phase-change ultrasound contrast agents with enhanced properties can be developed using direct emulsification of phospholipids in combination with fluorinated amphiphile diblocks as co-surfactant that self-assemble and play a significant role in the cohesiveness of the phospholipid based MB shells. Superheated perfluorobutane emulsions with semi-fluorinated co-surfactants were made with improved yield, stability, and shelf life compared to current acoustic droplet vaporization agents.

The compositions provided by the invention are therefore useful for a broad range of phase transition-assisted US theranostic platforms, for example the use of low boiling point perfluorocarbon NDs as PCCAs in ultrasonic diagnosis and treatment by enabling endothelial extravasation into tumor tissue. Compared to advocated MB condensation method, both stabilized and non stabilized ND compositions of the present invention provide more targeted NDs/cell and produce smaller aggregates in the circulation, avoiding potential plugging of small arteries and capillaries. Further, compositions of the invention comprising a nearly monodisperse ND diameter in the range of approximately 100 nm to 200 nm are capable of extravasating to perfuse tumor cells outside the vasculature.

III. Perfluorocarbon Nanodroplets

Acoustic droplet vaporization (ADV) of superheated perfluorocarbon (PFC) nanodroplets (NDs) demonstrates potential as an extravascular ultrasound contrast agent for facilitating ultrasound-based therapeutic applications, yet these agents are metastable and difficult to manufacture in high yield. The present inventors have shown that specific emulsification techniques and a surfactant/co-surfactant strategy improve the yield, stability, and shelf life of these agents.

In certain embodiments, the invention provides emulsions of perfluorobutane obtained through direct high-pressure homogenization combined with semi-fluorinated amphiphiles as co-surfactants. In certain embodiments, the invention provides emulsions of octafluoropropane obtained through direct high-pressure homogenization. Compositions of the invention were characterized using particle counters and sizers, and their acoustic response investigated with an Acuson Sequoia C512 ultrasound system with 15L8 transducer.

The formulation and emulsification methods of the invention result in several unique properties, such as: 1) sub-300 nm NDs with narrow size distribution (PDI <0.2); 2) high particle count (>10$^{12}$ NDs/mL); 3) high stability over weeks of storage at 4° C.; and 4) stability at ≥37° C. without spontaneous phase transition to MBs until exposed to ultrasound at moderate power (≥0.40 for DFB or ≥0.15 or OFP NDs). In certain embodiments, ND compositions provided by the invention exhibit no significant changes in size or concentration over a period of at least 50 h when stored at room temperature. As used herein, "no significant change in size" refers to a change of less than 10%, for example less than 5%, or less than 1% in average particle diameter. As used herein, "no significant change in concentration" refers to a change of less than 20%, for example less than 10%, or less than 5% in concentration.

When the NDs phase transitioned to MBs they produced a high contrast-to-noise ratio using standard B-mode imaging at diagnostic MI.

While methods of producing PEC droplets with high boiling points have been previously developed, the PFC NDs of the invention exhibit low boiling points to allow for a phase transition to MBs at physiological temperatures, thereby enhancing contrast in imaging applications. The invention therefore provides stabilized ND compositions comprising low-boiling point PFC NDs.

Conventional methods of producing PFC droplets using low-boiling point PEC require the production of MBs from standard lipids using sonication or high-speed mechanical agitation. The MBs are then compressed to be condensed into nanodroplets. MB condensation methods result in polydisperse ND compositions and batch to batch variability. This less efficient approach results in polydisperse NDs exhibiting lower particle count and a lack of stability at body temperature wherein the NDs spontaneously convert to MBs.

Previous attempts to produce PFC NDs with small particle sizes have resulted in an increase in the boiling point of an ND as the particle size was reduced. Thus, prior to the present disclosure, ND compositions having average particle diameters below approximately 1 µm produced a reduced number of MBs for a given pressure. In addition, conventional ND compositions have exhibited a higher rate of recondensation of vaporized, droplets, leading to a decreased number of MBs providing contrast for imaging. The stabilized ND compositions of the present invention overcome these limitations in the art by providing stabilized low-boiling point NDs with significantly reduced diameters compared to conventional PFC droplets. In certain embodiments, the stabilized ND compositions provided by the invention exhibit monodisperse particle size with diameters in the range of approximately 100 nm to 300 nm, high concentrations in the range of approximately 10$^{12}$ NDs/mL and stability over extended periods at about 4° C.

The compositions and methods provided by the present invention therefore represent a significant advance in the field. For example, it was previously believed that it was not possible to prepare high quality DFB or OFP nanoemulsions following a direct, one-step method. However, the present inventors have remarkably shown that DFB and OFP nanoemulsions with beneficial properties can be produced using the methods of the present invention. In certain embodiments, temperature control over the span of the formulation is used to emulsify DFB or OFP into NDs, resulting in NDs with improved properties. In other embodiments, the introduction of semi fluorinated alkanes as co-surfactants improves stability at body temperature and allows a sharper transition from NDs to MBs with a more defined vaporization threshold.

IV. Surfactants

As used herein, the term "surfactant" refers to an amphiphilic phospholipid-based compound capable of encapsulating low boiling point perfluorocarbons in nanodroplets. Surfactants may include purified natural phospholipid derivatives and synthetic phospholipid derivatives. Improved stability is achieved by the addition of co-surfactant. Optimal stabilization is expected with surfactant and co-surfactant with lipid chain length that match with each other, for example C18: F8H18 and DSPC (18:0 PC); and DSPE-PEG.

V. Co-Surfactants

The present invention provides emulsions of PFC liquids to provide stabilized ND compositions having favorable properties for use as PCCAs. In certain embodiments, the invention provides emulsions of PFC liquid combined with a co-surfactant, for example a semifluorinated alkane. Co-surfactants useful in the present invention include linear FnHm diblocks with the general formula $C_nF_{2n+1}C_mH_{2m+1}$, for example n=8, m=18. n and m may vary depending on the surfactant used, for example n=5, 8, 10, and m=12, 16, 18, 20. When used in conjunction with phospholipids and because of their amphiphilic characteristics, fluorocarbon/hydrocarbon diblocks play the role of co-surfactant and provide unmatched stabilization of fluorocarbons in water emulsions. Despite their simple structure (an F-chain covalently attached to an H-chain), FnHm diblocks display unique properties due to both energetic and steric frustrations generated. FnHm diblocks are amphiphilic (different affinities: Fn portion is fluorophilic, hydrophobic and lipophobic, while Hm portion is lipophilic, hydrophobic and fluorophobic), amphisteric (Fn and Hm chains have different cross sections ~28 Å and ~19 Å respectively, different conformations and different space requirements) and amphidynamic (distinct dynamic regimes: Fn is stiff and rodlike with a twisted helical structure Hm is more flexible with a planar zigzag configuration).

VI. Methods of Producing Stabilized Nanodroplets

The invention further provides methods of producing the stabilized PFC nanodroplet, compositions provided by the invention, comprising low-boiling point nanodroplets with low particle size at high concentrations. In certain embodiments, methods provided by the invention include emulsion of a low-boiling point PFC with a semifluorinated alkane. In further embodiments, emulsion comprises use of a homogenizer, for example a high-pressure homogenizer. In some embodiments of the invention, emulsion is carried out at temperatures below 0° C., for example at about −20° C. or at about −35° C.

In exemplary embodiments, stabilized nanodroplets may be obtained using methods comprising the steps listed below and described, herein. A person of skill in the art will readily understand that that modifications and variations are possible and within the scope of the invention. Such modifications include variations in phospholipid composition, temperatures, and pressures.

Step 1) Dissolution of the phospholipid mixture in the excipient solution. In certain embodiments, the excipient mixture comprised 1,2-distearoyl-sn-glycero-3-phosphocholine (DSPC) and 1,2-distearoyl-sn-glycero-3-phosphoethanolamine-N-methoxy(polyethylene-glycol)-2000 (DSPE-PEG2000) in a 9:1 molar ratio. Minor modifications in the phospholipid composition (both structures and molar ratio) will not affect the quality of the emulsion. Alternative phospholipids and lipids investigated were: 1,2-distearoyl-sn-glycero-3-phosphoethanolamine-N-methoxy(polyethylene-glycol)-5000 (DSPE-PEG5000), 1,2-distearoyl-sn-glycero-3-phosphoethanolamine-N-[maleimide(polyethylene glycol)-2000] (DSPE-PEG2000-Mal), 1,2-distearoyl-sn-glycero-3-phosphoethanolamine-N-[maleimide(polyethylene glycol)-5000] (DSPE-PEG5000-Mal) and 1,2-distearoyl-3-trimethylammonium propane (DSTAP). In certain embodiments, the excipient solution comprised PBS 1X, propylene glycol, and glycerol (16:3:1) or propylene glycol and PBS 1X (6:4). Total phospholipid concentration may range from 1-3.5 mg/mL to give stable emulsions. Typically, the sample was warmed up at 70° C. for 5-15 min followed by 5-15 min of bath sonication at 65° C. to 70° C. in degassed water until the dispersion is clear.

Step 2) Cooling down of the phospholipid mixture. In certain embodiments, the glass vial containing phospholipid dispersion at 70° C. was placed in a −20° C. ice bath for 2 min transferred in a 3 mL syringe and kept in the ice bath for one additional minute. Alternatively, the phospholipid dispersion can be transferred into the syringe and cooled down until a sample temperature between −15° C. and −20° C. In certain embodiments, the phospholipid dispersion was directly transferred in a 3 mL syringe and cooled down for 3 min in a −72° C. ethanol-dry ice bath.

Step 3) Addition of liquid PFC. In certain embodiments, PFC was directly condensed in a 1 mL syringe cooled down in a dry ice bath. In certain embodiments, PEC was condensed in a glass vial cooled down at −72° C. in a dry ice/ethanol bath prior transfer to a 1 mL syringe cooled down in the same cooling bath.

Step 4) Direct emulsification through direct high-pressure homogenization. In certain embodiments, 150 µL of liquid PFC was introduced into the lipid solution and directly injected in the high pressure homogenizer (9 cycles at a 13,000 psi) using a Low Volume Microfluidizer (LV1, Microfluidics) with both coil and tray cooled with ice and sodium chloride (T=−15 to −20° C.). In certain embodiments, 100 µL of liquid PEC was introduced into the lipid solution and directly injected in the high pressure homogenizer (9 cycles at a 13,000 psi) using a Low Volume Microfluidizer (LV1, Microfluidics) with both coil and tray cooled with ice, sodium chloride, dry ice and ethanol (T=−30 to −35° C.). In certain embodiments, the syringe was centrifuged for 1 to 2 min at 250 g and the resulting emulsion was stored at −20° C. or 4° C.

In certain embodiments, PFC emulsions were obtained through high pressure homogenization at pressures between 2,000 psi and 13,000 psi to give stable emulsions. High pressure homogenization may, in some embodiments, occur at pressures of 2,000, 2,500, 3,000, 3,500, 4,000, 4,500, 5,000, 5,500, 6,000, 6,500, 7,000, 7,500, 8,000, 8,500, 9,000, 9,500, 10,000, 10,500, 11,000, 11,500, 12,000, 12,500, or 13,000 psi or any range comprising these, such as between 2,000 and 13,000, between 2,500 and 13,000, between 3,000 and 13,000, between 3,500 and 13,000, between 4,000 and 13,000, between 4,500 and 13,000, between 5,000 and, 13,000, between 5,500 and 13,000, between 6,000 and 13,000, between 6,500 and 13,000, between 7,000 and 13,000, between 7,500 and, 13,000, between 8,000 and 13,000, between 8,500 and 13,000, between 9,000 and 13,000, between 9,500 and 13,000, between 10,000 and 13,000, between 10,500 and 13,000, between 11,000 and 13,000, between 11,500 and 13,000, between 12,000 and 13,000, between 12,500 and 13,000, between 2,000 and 12,500, between 2,000 and 12,000, between 2,000 and 11,500, between 2,000 and 11,000, between 2,000 and 10,500, between 2,000 and 10,000, between 2,000 and 9,500, between 2,000 and 9,000, between 2,000 and 8,500, between 2,000 and 8,000, between 2,000 and 7,500, between 2,000 and 7,000, between 2,000 and 6,500, between 2,000 and 6,000, between 2,000 and 5,500, between 2,000 and 5,000, between 2,000 and 4,500, between 2,000 and 4,000, between 2,000 and 3,500, between 2,000 and 3,000, and between 2,000 and 2,500. Attempts to prepare NDs at 23,000 psi resulted in non-stable emulsion, most likely due to the elevation in temperature generated at high pressure that cannot be counteracted with the salt water bath to stay below DFB boiling point.

In further embodiments, PFC emulsions were obtained at temperatures between −15° C. and −35° C. producing stable emulsions. No freezing was observed at −20° C. (PBS 1X:propylene glycol:glycerol in a 16:3:1 ratio). No freezing was observed at −35° C. (propylene glycol:PBS 1X in a 6:4 ratio).

VII. Applications of Stabilized Nanodroplets

Stabilized ND compositions of the present invention exhibit low boiling points, small particle size, higher concentration, and improved stability compared with previously known ND compositions. These properties allow for improved performance in ultrasound imaging and therapeutic applications.

In certain embodiments, the stabilized ND compositions of the present invention are useful in ultrasound imaging methods. Compositions provided by the invention exhibit stability at physiological temperatures without spontaneous vaporization and conversion to MBs. However, compositions of the invention vaporize to MBs when exposed to ultrasound at moderate power, allowing for controlled activation of the compositions for use as contrast agents in ultrasound imaging.

The small particle size of the compositions of the invention allows for targeting to extravascular sites, endothelial cells, and stem cells, and further allows for the accumulation of high particle counts in tissue, which is not accessible to larger particles. The ability of the disclosed stabilized ND compositions to access a variety of tissue types is further useful in the therapeutic use of nanodroplets, for example in delivering pharmaceutical or gene therapies to cells. In one embodiment, the improved stability of the compositions provided herein allows passive accumulation of nanodroplets in tissue, for example tumor tissue. Additionally NDs can be used as contrast agents for imaging guided therapy, non-invasive pressure estimation, blood-brain barrier opening, sonoporation, blood clot ablation, or therapeutic embolization.

EXAMPLES

Example 1

Production of Non-Stabilized and Stabilized Decafluorobutane Nanodroplets

Monodisperse decafluorobutane nanodroplets were formulated by dissolution of DSPC and 1,2-distearoyl-sn-glycero-3-phosphoethanolamine-N-methoxy(polyethyleneglycol)-2000 (DSPE-PEG2000) in a 9:1 molar ratio at a total lipid concentration of 3.5 mg/mL. Lipids were purchased from Avanti and Corden Pharma, and decafluorobutane purchased from F2 Chemicals Ltd. The excipient solution was comprised of PBS 1X, propylene glycol and glycerol in a 16:3:1 v/v/v ratio. Dry lipid film was dispersed in the excipient solution at 70° C. for 15 min followed by 15 min of bath sonication at 68° C. (Branson) in degassed water. The resulting; sample was cooled down for 2 min in a −20° C. ice bath, transferred in a 3 mL syringe and kept in the ice bath for 1 additional minute. DFB was condensed by flowing DFB gas into a 1 mL syringe cooled in dry ice until 150 µL of liquid DFB is recovered. Upon addition of 150 µL of liquid DFB into the lipid solution, the DFB emulsion was obtained through direct high-pressure homogenization (9 cycles at 13,000 psi) using a Low Volume Microfluidizer (LV1, Microfluidics) with both cooling coil and tray cooled with ice and sodium chloride. Finally, the syringe was centrifuged for 2 min at 250 g and the resulting emulsion was stored at 4° C. Illustrative photographs are presented in FIG. 1A. F8H18 stabilized NDs samples were prepared using an equimolar amount of diblock co-surfactant with respect to the phospholipid content.

In alternative experiments, prior to transfer to the syringe, the lipid solution was cooled down for 2 min at −20° C. ice bath, 150 µL of liquid DFB transferred in the vial, and the resulting mixture was transferred in a 3 mL syringe.

It was further shown that specific functionalities can be incorporated into the outer surface of the ND's shell. DFB NDs were fabricated using DSPE-PEG functionalized with maleimide end groups followed by the coupling with targeting ligand (proteins, antibodies, peptides) using a thiol-maleimide coupling. As long as the shell presents a reactive group on the outer surface, any coupling chemistry is available (coupling with dyes, thiolated molecules, drugs). Formulations can be purified by centrifugation without significant loss (>50% recovery after 20 minutes at 400 g) which assure the best purity of the functionalized NDs. Formulations can be frozen and thawed without significant loss of concentration.

Synthesis of F8H18

Briefly, F8H18 was synthesized in a 2-step procedure, starting from the addition of the perfluorooctyliodide to 1-octadecene, followed by a treatment with zinc powder to reduce the iodine-containing adduct. Finally, F8H18 was purified by repeated crystallizations from methanol.

Perfluorooctyliodide (328 mg, 0.6 mmol, 0.16 mL), NaHCO$_3$ (43.1 mg, 0.05 mmol) and 85% Na$_2$S$_2$O$_4$ (103 mg, 0.5 mmol) were added at 0° C. to a solution of 1-octadecene (127 mg, 0.05 mmol, 0.16 mL) in acetonitrile (2.5 mL) and deionized water (0.5 mL) under argon. The reaction mixture was stirred for 4 h at room temperature. The resulting mixture was diluted with deionized water and extracted with dichloromethane (DCM). Organic layers were washed with brine and then dried with MgSO$_4$ and filtered. After filtration and evaporation of the solvent, the residue was dissolved in glacial acetic acid (1.5 mL), then zinc dust was added (98.8 mg, 1.5 mmol) and the reaction mixture was stirred at room temperature overnight under argon. The zinc slurry was triturated with DCM, filtered and the solvents were removed under reduced pressure. The residue was purified by three successive recrystallizations in methanol to yield the desired compound as a white waxy solid (281 mg, 84% over 2 steps).

Example 2

Production of Non-Stabilized Octafluoropropane Nanodroplets

Figure 1B:
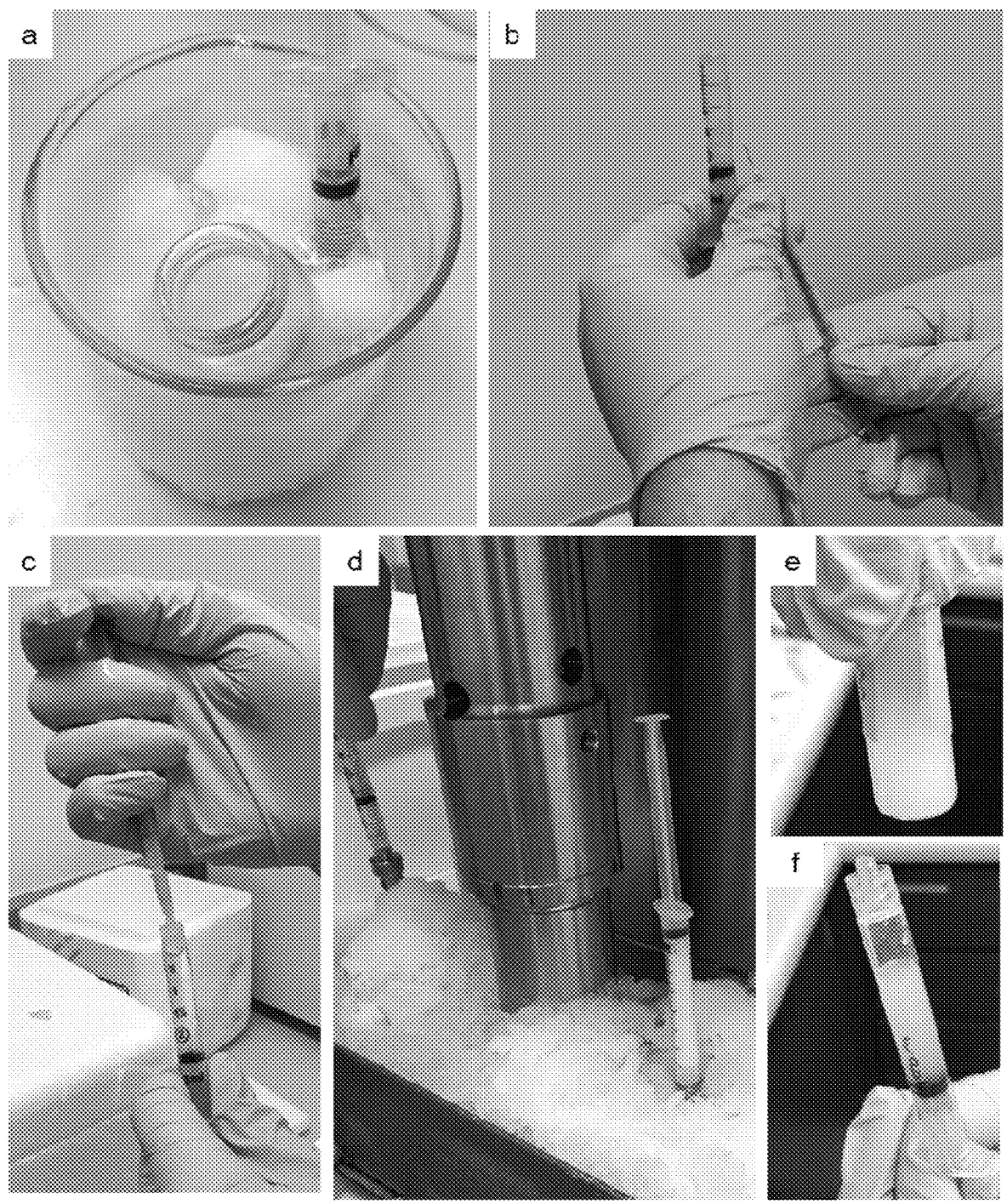
FIG. 1B shows an illustrative representation of exemplary OFP ND production steps: (panel a) OFP gas condensed by cooling at −70° C. with an ethanol-dry ice bath. Syringe containing clear lipid film dispersed in excipient (propylene glycol/water 60:40) cooled down in the same cooling bath. (panel b) 100 uL of liquid OFP measured with a 1 mL syringe and (panel c) liquid OFP transfer into the sample syringe. (panel d) Emulsification using the LV1 microfluidizer cooled at −35 C using a sodium chloride/ice/dry ice cooling bath. (panel e) Milky solution obtained after nine passes at 13,000 Psi. (panel f) Additional sample obtained by washing the system with 1.5 mL excipient.

Monodisperse octafluoropropane nanodroplets were formulated by dissolution of DSPC and 1,2-distearoyl-snglycero-3-phosphoethanolamine-N-methoxy(polyethyleneglycol)-2000 (DSPE-PEG2000) in a 9:1 molar ratio at a total lipid concentration of 3.5 mg/mL. Lipids were purchased from Avanti and Corden Pharma, and octafluoropropane (OFP) purchased from F2 Chemicals Ltd. The excipient solution was comprised of propylene glycol and PBS 1X in a 6:4 v/v ratio. Dry lipid film was dispersed in the excipient solution at 70° C. for 5 min followed by 15 min of bath sonication at 68° C. (Branson) in degassed water. The resulting sample was transferred in a 3 mL syringe and cooled down for 3 min in a −72° C. in an ethanol/dry ice bath. OFP was condensed by flowing OFP gas into a glass vial cooled at −72° C. in an ethanol/dry ice bath until 100 μL liquid DFB was recovered. Upon addition of 100 μL of liquid OFP into the lipid solution, the emulsion was obtained through direct high-pressure homogenization (9 cycles at a 13,000 psi) using a Low Volume Microfluidizer (LV1, Microfluidics) with both coil and tray cooled at −35° C. with a mixture of ice, sodium chloride, dry ice, and ethanol. Finally, the syringe was centrifuged for 2 min at 250 g and the resulting emulsion was sized stored at −20° C. (DLS: Z-average <200 nm, PDI=0.29; TRPS: Mean Diameter=170±60 nm, d90=230 nm, concentration ~$2.10^{10}$ NDs/mL). Illustrative photographs are presented in FIG. 1B.

Example 3

Size Distribution of Non-Stabilized and Stabilized Decafluorobutane Nanodroplets Emulsion conducted using a high pressure homogenizer at −20° C. yielded highly monodisperse, stable emulsions with a high concentration of stabilized NDs as measured by tunable resistive pulse sensing (TRPS) and dynamic light scattering (DLS), as shown in Table 1. Table 1 shows DFB ND distribution statistics using DLS (N=3, n=3) and TRPS (N=2, n=3) ±SD. $d_{90}$ or 90th percentile is the diameter value for which 90% of the distribution have a diameter below this value.

TABLE 1

|  | DLS | | TRPS | | |
| --- | --- | --- | --- | --- | --- |
|  | $Z_{avg}$ (nm) | PDI | Mean Diam.(nm) | $d90^a$ | Concentration (#/mL) |
| DFB only | 294 ± 20 | 0.16 | 282 ± 28 | 416 ± 71 | $1.33 \times 10^{12} \pm 0.36$ |
| OFP only | 199 ± 10* | 0.27 | 210 ± 30** | 298 ± 63 | $5.16 \times 10^{10} \pm 3.6$ |
| DFB + F8H18 | 247 ± 9 | 0.14 | 213 ± 15 | 323 ± 24 | $1.27 \times 10^{12} \pm 0.119$ |

$^a d_{90}$ or $90^{th}$ percentile is the diameter value for which 90% of the distribution have a diameter below this value.
*N = 3, n = 1.
**N = 2, n = 1.

Figure 2:
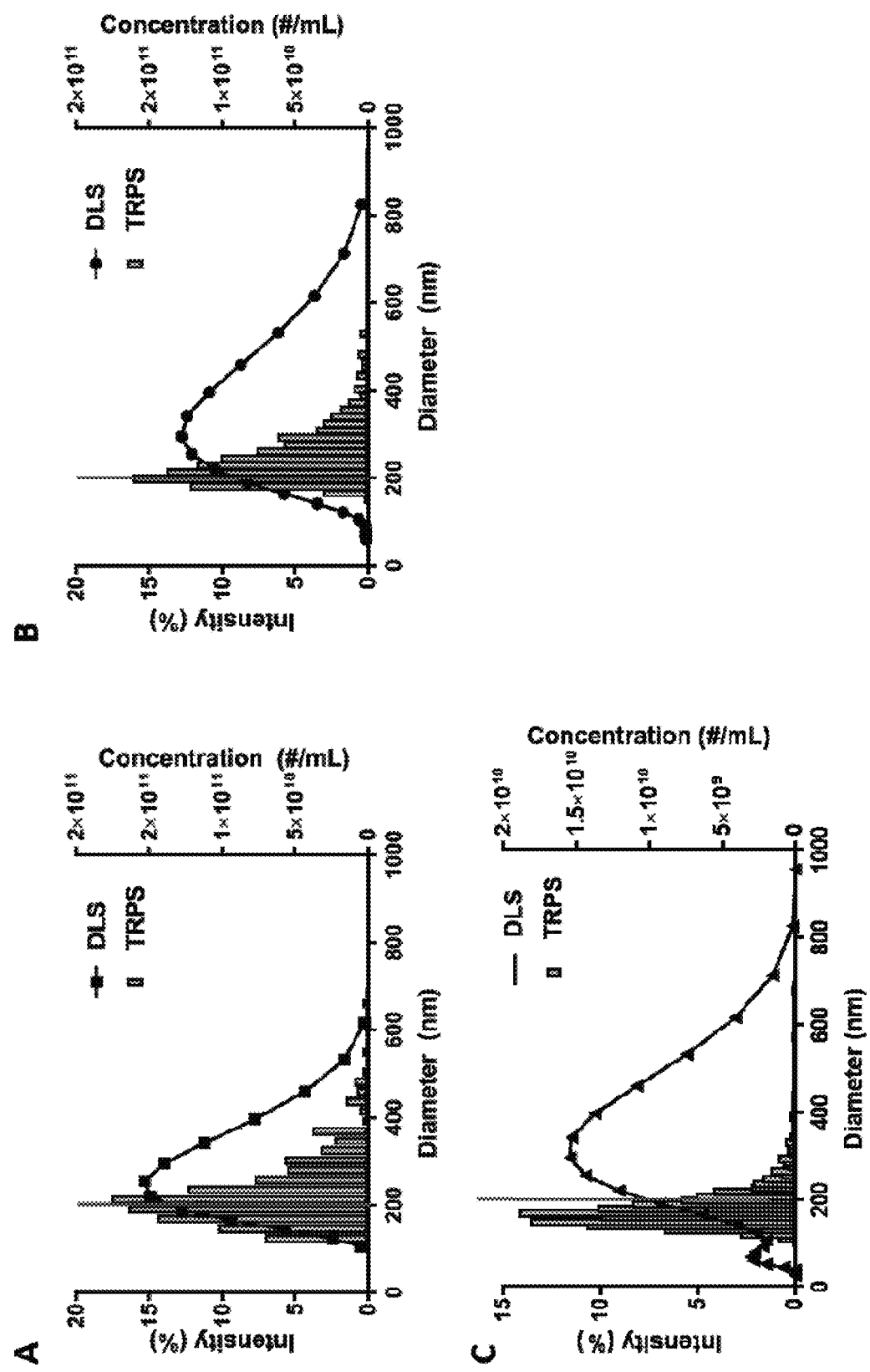
FIG. 2 shows size distributions of decafluorobutane (DFB) and octafluoropropane (OFP) nanodroplets measured by Tunable Resistive Pulse Sensing (TRPS, histograms, concentration in number of nanodroplets/mL) and Dynamic Light Scattering (DLS, solid lines, intensity in %). (panel A) DFB nanodroplets (NDs) stabilized with the semifluorinated alkane F8H18, (panel B) non-stabilized DFB NDs and (panel C) non-stabilized OFP NDs produced by high pressure homogenizer. Red lines were drawn at 200 nm to emphasize the larger population of ND below 200 nm in the stabilized sample. Panel D shows size distributions (weighted by intensity, volume and number), and correlation functions of non-stabilized DEB NDs when in coexistence with Definity MBs (1, 10 and 50%). Panel E shows representative non-stabilized DFB ND emulsion size distributions measured by TRPS (concentration in NDs/mL) as a function of counting events (500, 10002000, and 3000).
Figure 2:
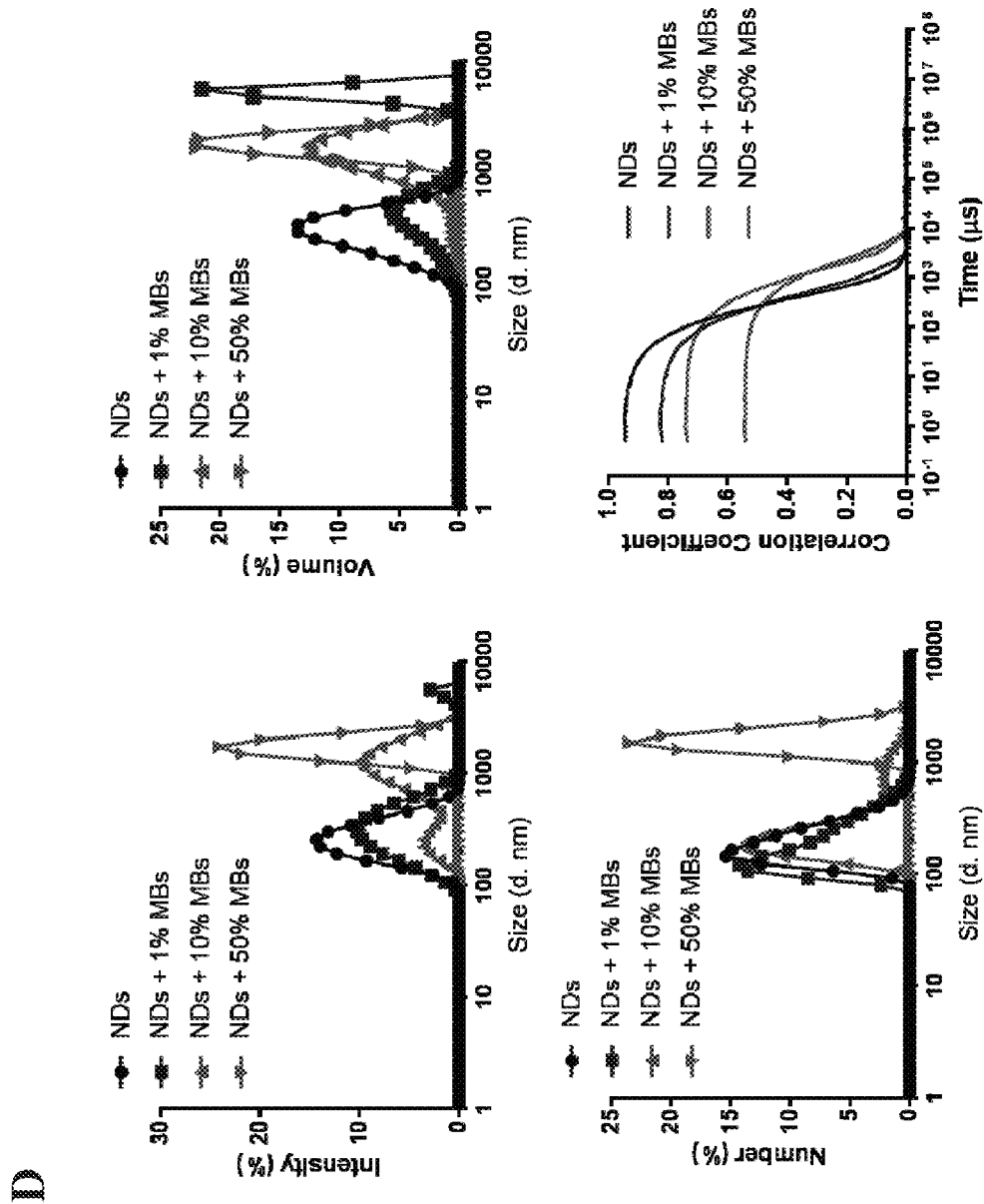
Figure 2:
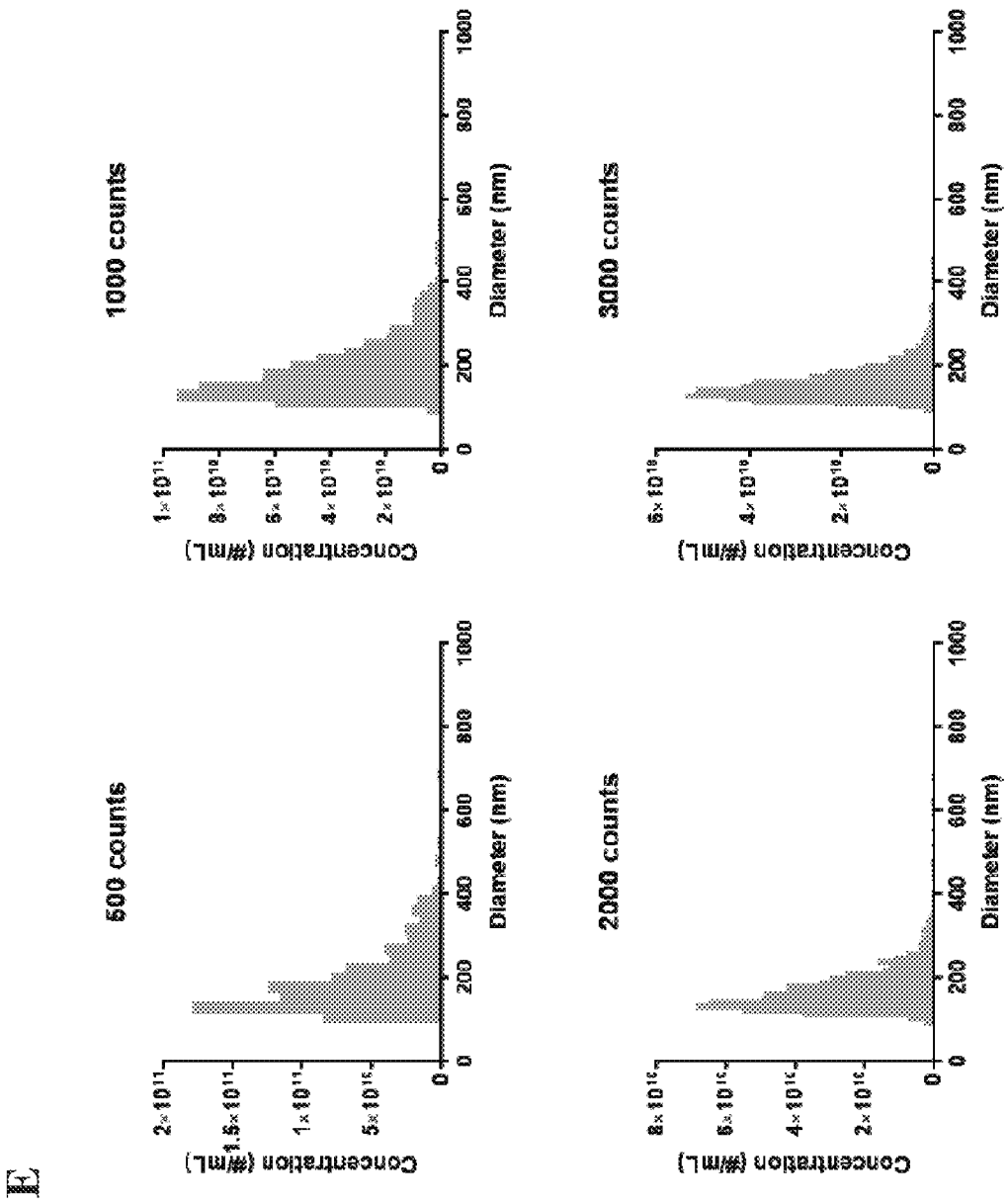
Figure 3A:
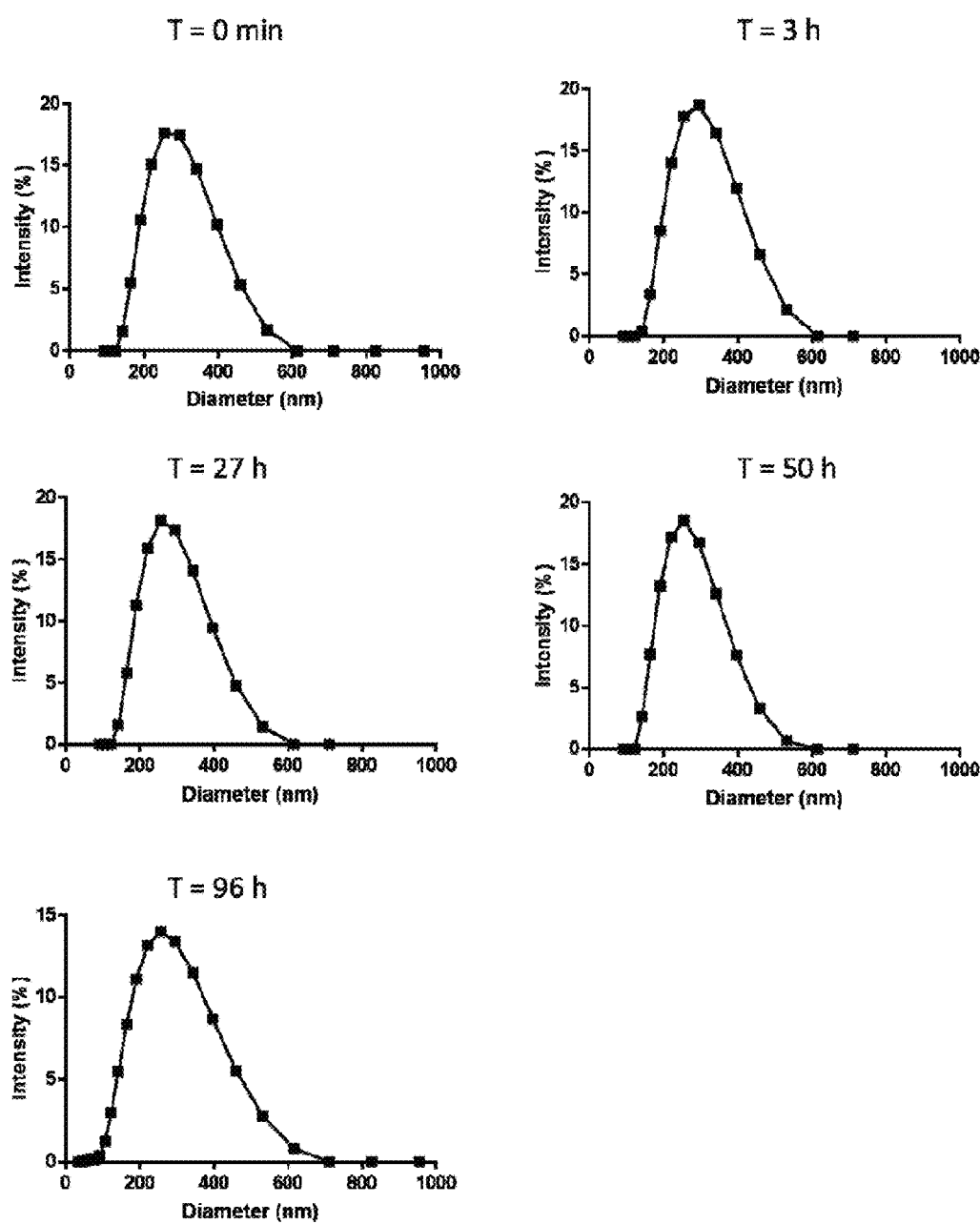
FIG. 3A shows size distributions (DLS) over 96 h of storage at room temperature of non-stabilized DFB nanodroplets.
Figure 3B:
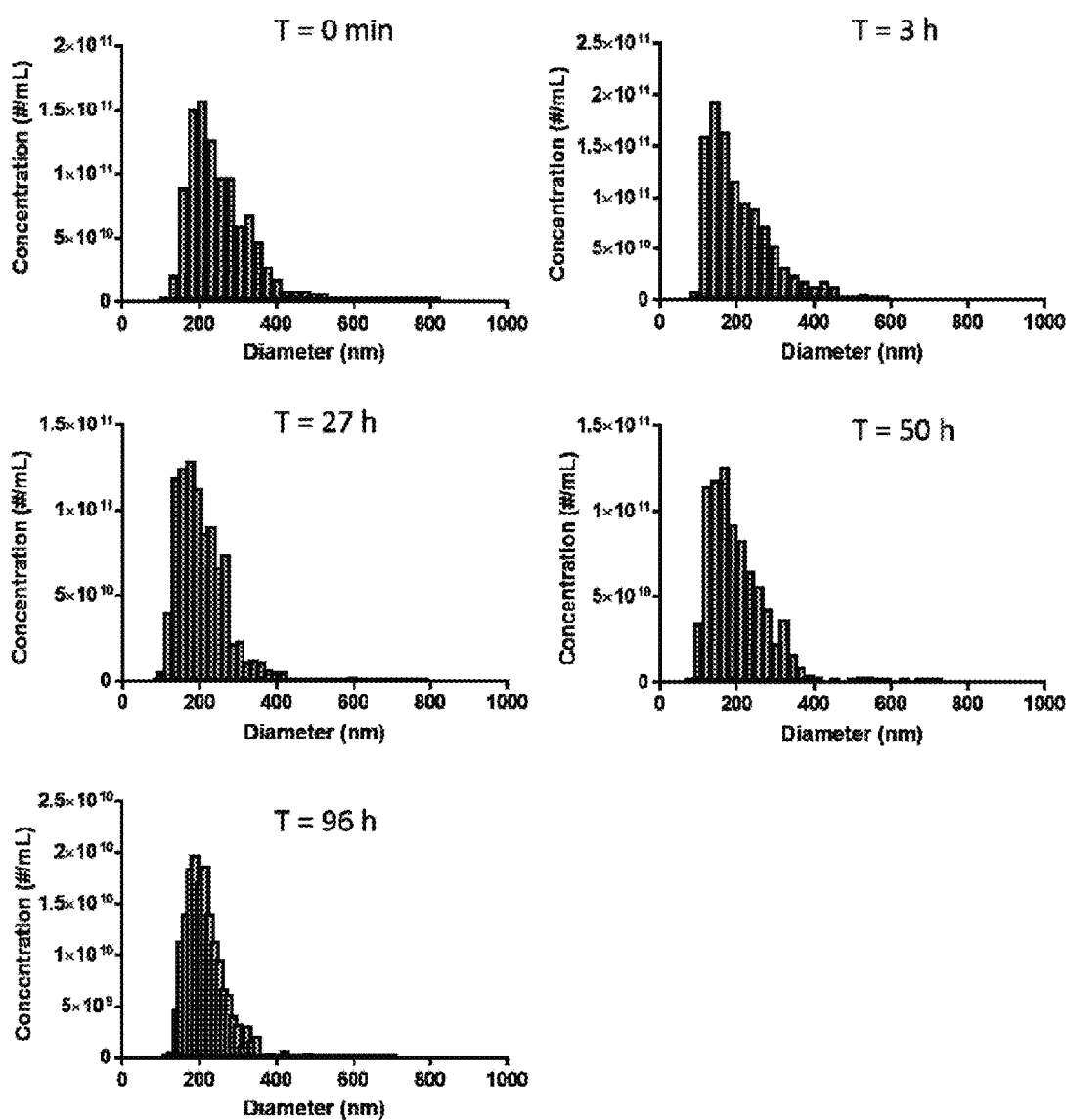
FIG. 3B shows mean diameters (TRPS) over 96 h of storage at room temperature of non-stabilized DFB nanodroplets.
Figure 3C:
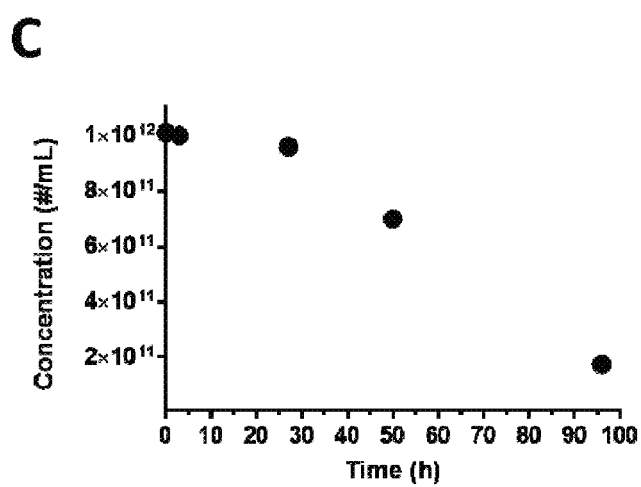
FIG. 3C shows concentrations (TRPS) over 96 h of storage at room temperature of non-stabilized DFB nanodroplets.

DLS showed that although all samples were monodispersed in size, there were consistently decreases in hydrodynamic diameter and polydispersity index (PDI) upon the introduction of F8H18 the formulation (247±9 nm and 0.14 vs. 294±20 nm and 0.16 with and without co-surfactant respectively) (Table 1 and FIG. 2A-C, lines). The size distribution of the ND emulsions was also analyzed by tunable resistive pulse sensing (TRPS, Table 1 and FIG. 2A-C, bars). TRPS allows single particle measurements as NDs are driven through pores one at a time and provide accurate size and concentration determinations. Samples containing F8H18 appeared to present smaller mean diameters (213±15 nm vs. 282±28 nm and SD=41 vs. 58 nm with and without co-surfactant respectively). F8H18 stabilized NDs showed lower d90 values: 90% of the distribution have a diameter below 323±24 nm, while samples that do not contain F8H18 have an average d90 value of 416±71 nm. As expected. F8H18 diblock incorporated in the emulsion formulation provide a tighter packing by reducing the area occupied by the PL at the droplets' surface, resulting in smaller ND sizes.

While DLS is not useful for measuring microbubbles or multimodal particle populations, the fact that a single nearly normally distributed peak was observed suggests the absence of microbubbles in the emulsion sample. Positive controls consisting of NDs in coexistence with various concentration of Definity MBs (1, 10 and 50%) confirmed that DLS pick up the peak associated with the MBs in addition to the NDs (FIG. 2D). TRPS was done with 500, 1000, 2000 and 3000 counting events (FIG. 2E) and the fraction of the population with diameters greater than 500 nm was measured. While large droplets will likely contribute the most to thermal instability due to their lower Laplace pressure, they did not represent more than 0.9±0.3% of the droplet count (n=3).

Example 4

Figure 4:
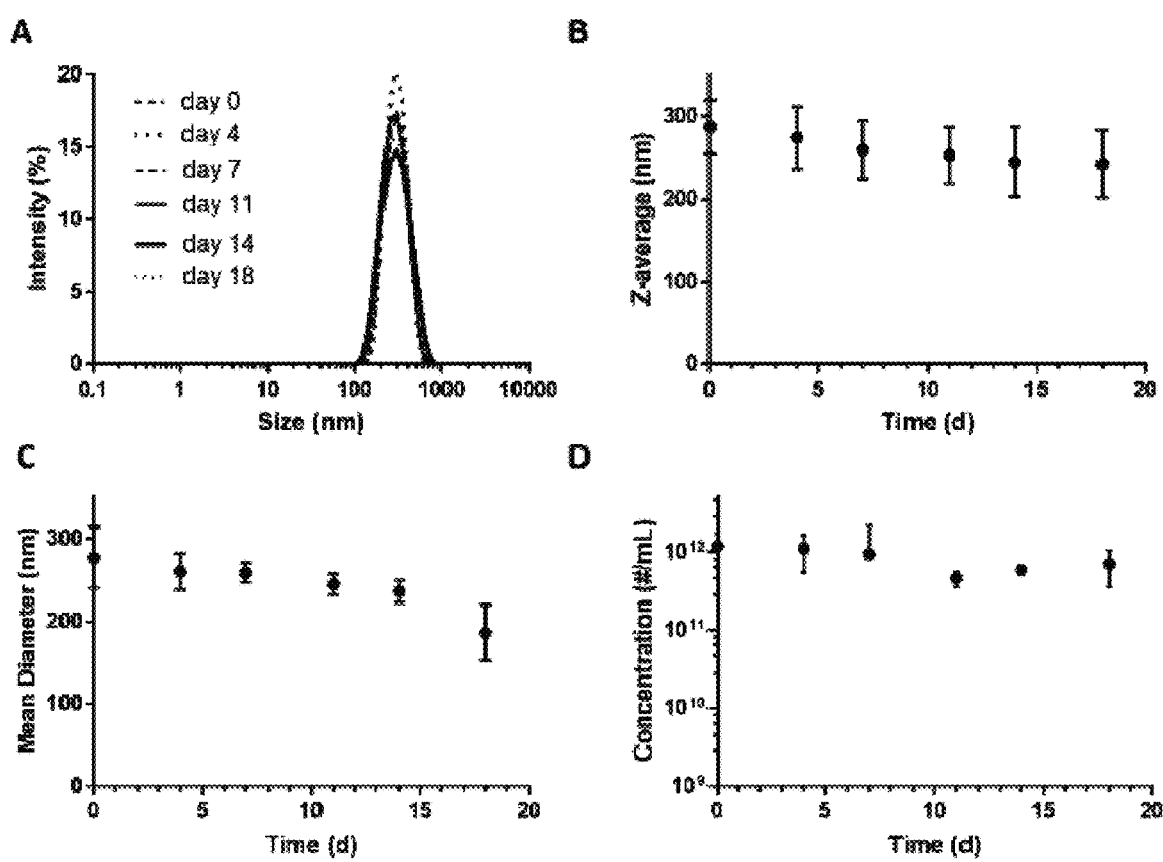
FIG. 4 shows the stability of non stabilized DFB ND emulsions stored at 4° C. over 18 days. Size distribution (panel A) and Z-average (panel B) measured by DLS, and mean diameter (panel C) and concentration (panel D) measured by TRPS.
Figure 5:
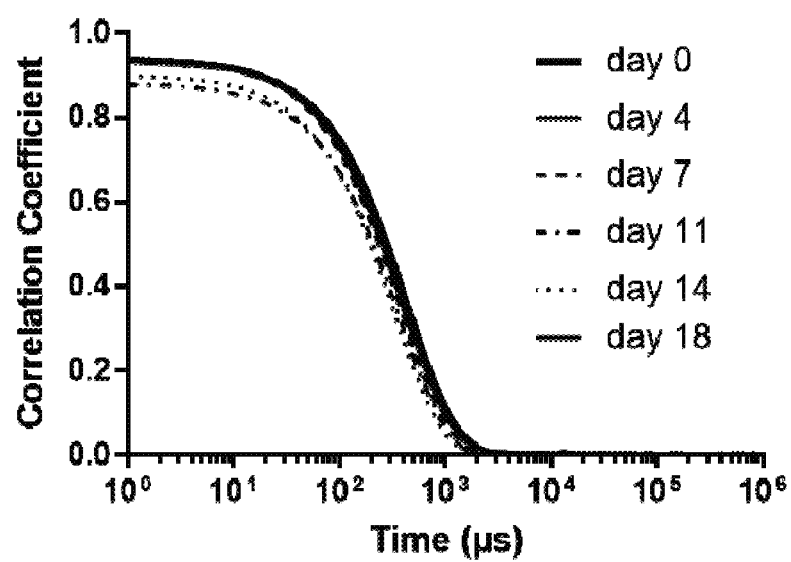
FIG. 5 shows the representative correlation functions of non stabilized DEB NDs over an 18-day observation period. A smooth, single exponential decay functions confirm the presence of mono-size particle dispersions.
Figure 6:
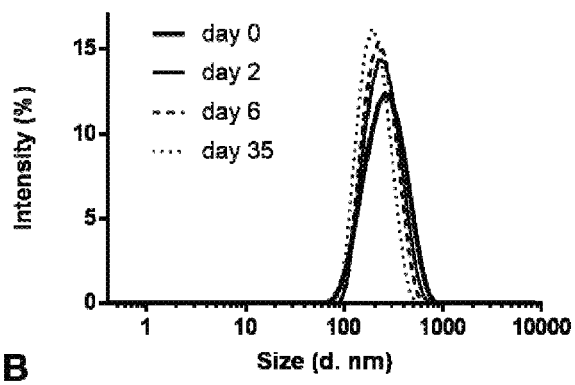
FIG. 6 shows (panel A) size distribution (DLS), (panel B) $Z_{avg}$ and derived count rate (DLS) over 35 days and (panel C) correlation curves of F8H18 stabilized DFB nanodroplets emulsions over 35 days of storage at 4° C.
Figure 6:
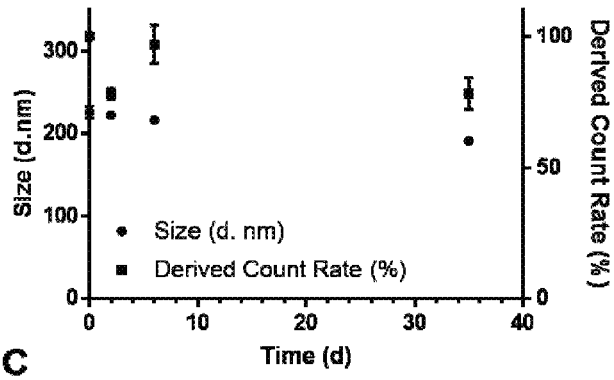
Figure 6:
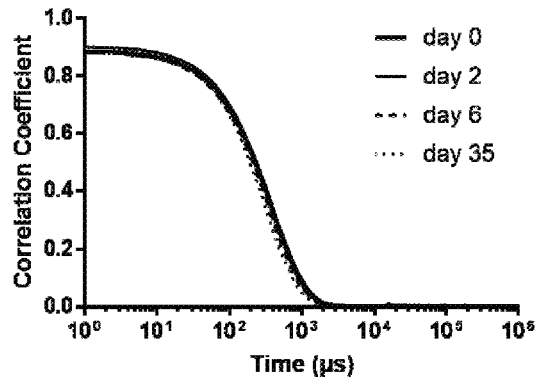

Stability at 4° C. and 22° C. of Non-Stabilized and Stabilized Decafluorobutane Nanodroplets Storage stability is an essential requirement for DFB-in-water nanoemulsions to be of practical use. Non-stabilized NDs were stable after at least 24 h at 22° C. (FIG. 3A-C and FIG. 9A-B) and at least 18 days of storage at 4° C. (FIGS. 4 and 5) as measured by dynamic light scattering (DLS) and tunable resistive pulse sensing (TRPS) respectively. Stabilized NDs were stable after 35 days of storage at 4° C. as measured by DLS (FIG. 6). At 4° C. no significant changes in size, derived count rate and concentration were observed, as shown in FIG. 5 (Non-stabilized NDs) and 6 (Stabilized NDs). DLS confirms the complete absence of micron-sized MBs. No fluctuations in the correlation coefficient curve in terms of Y intercept, exponential decay lifetime, and baseline quality were observed. These results are consistent with the absence of large particles, aggregates or multimodal distribution. As mentioned above, some variations in the concentrations determined by TRPS are most likely due to the fact that different nanopores have been used over time. When not specified, DLS data are intensity weighted.

Example 5

Figure 7:
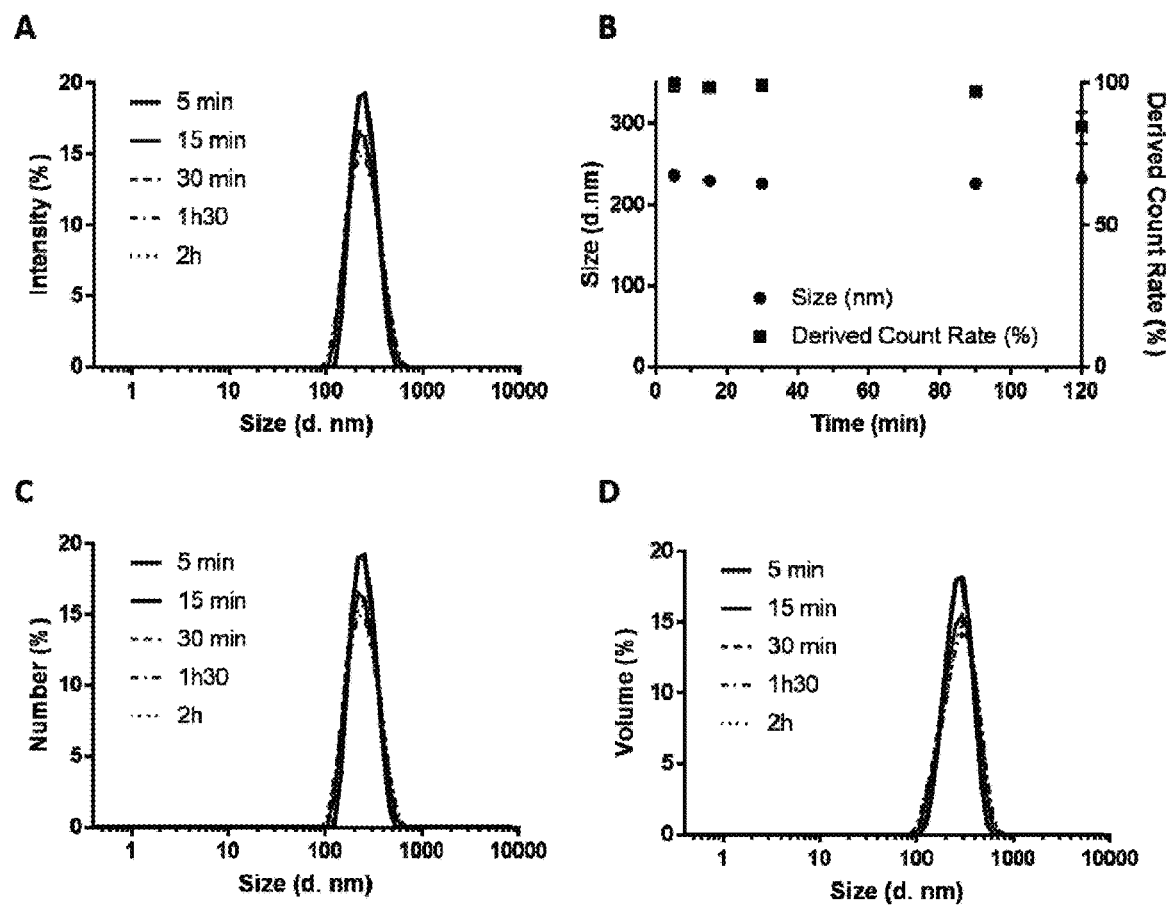
FIG. 7 shows (panel A) intensity-weighted size distribution, (panel B) $Z_{avg}$ and derived count rates, (panel C) number-weighted size distribution, (panel D) volume-weighted size distribution of ND emulsions with no F8H18 over 2 h incubation at 37° C.
Figure 8:
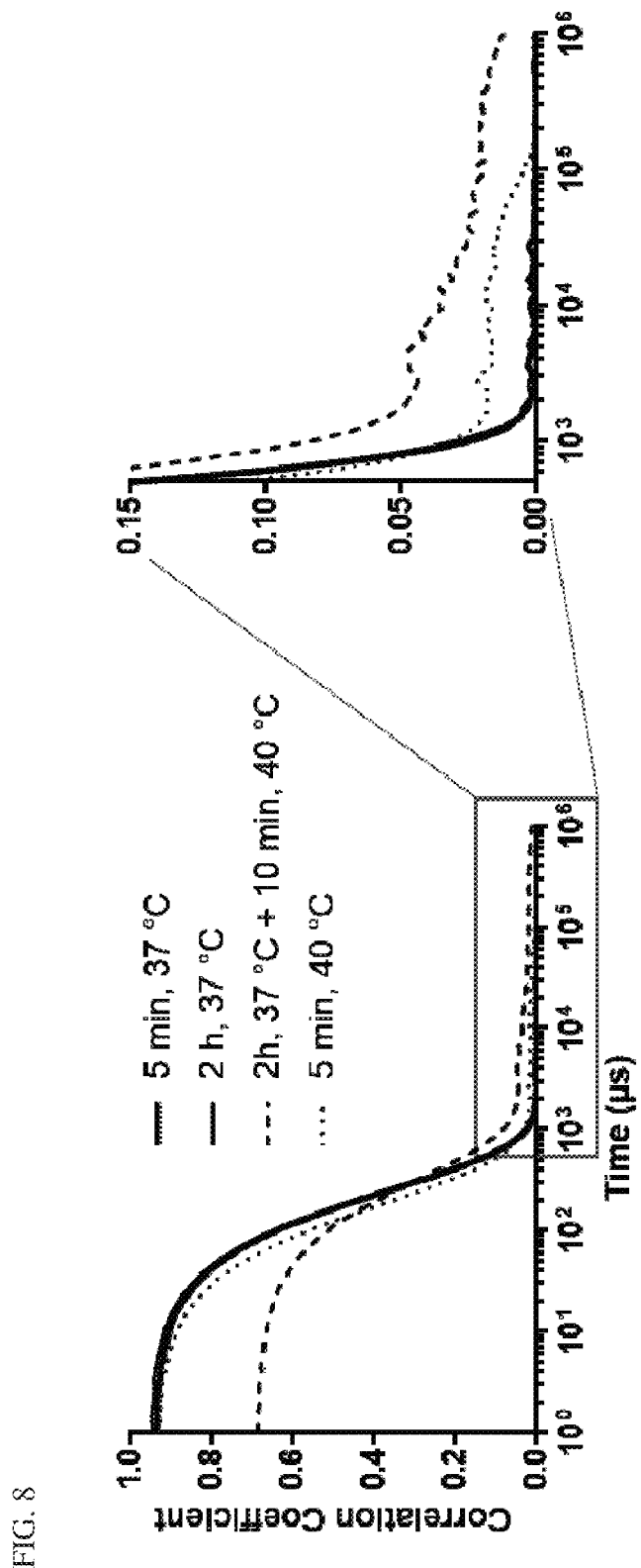
FIG. 8 shows correlation curves of non-stabilized. DFB NDs at different temperatures.
Figure 9:
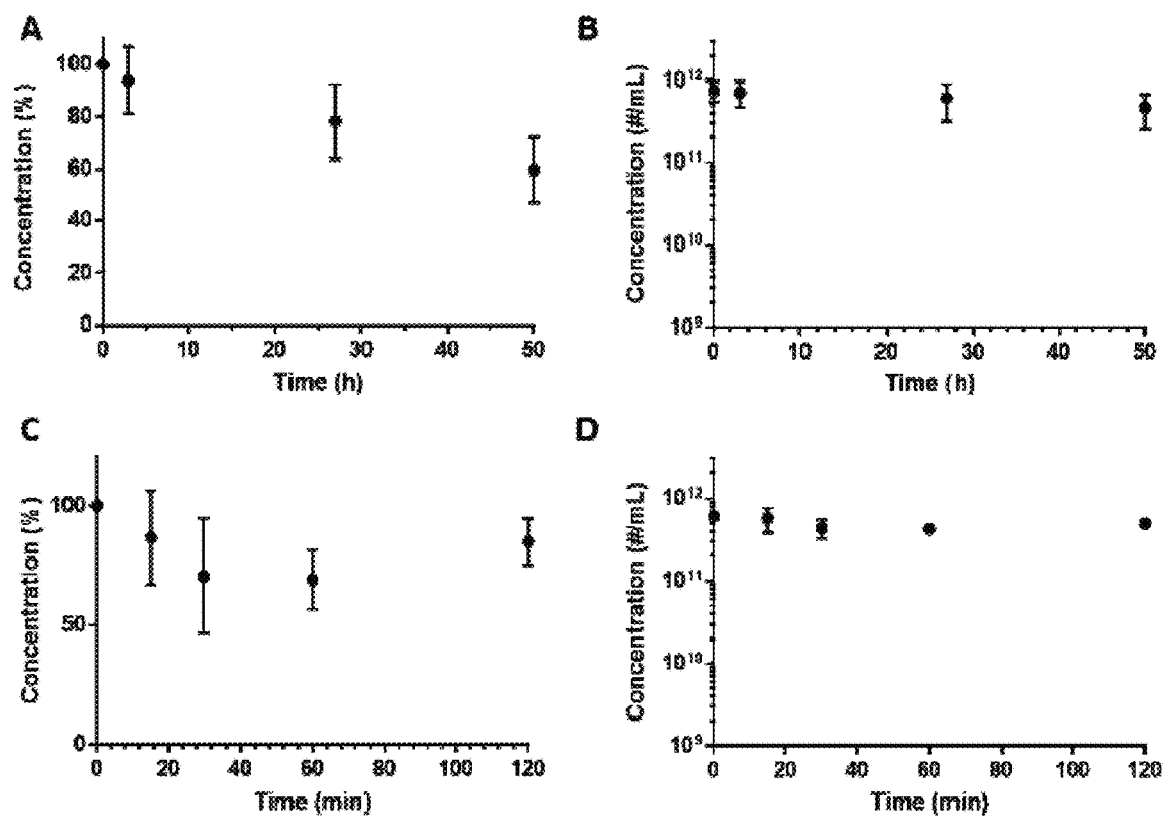
FIG. 9 shows non-stabilized NDs concentrations determined by TRPS as a function of incubation time at room temperature (22° C.) (panels A and B) and physiologic temperature (37° C.) (panels C and D).

Thermal Stability of Non-Stabilized and Stabilized Decafluorobutane Nanodroplets In addition to their stability at low temperatures for extended periods as assessed by DLS, non-stabilized NDs exhibit optimal stability at 37° C. over a period of at least 2 h with no changes in size distribution by DLS (distribution weighted by intensity, volume and number; FIGS. 7A, C, and D), derived particle count rate (FIG. 7B) and concentration (measured by TRPS, FIG. 9 C-D). While no decreases in concentration or changes in size were observed at 37° C., the non-stabilized ND sample showed some instability at 40° C., with the appearance of MBs and liposomes. This destabilization was also confirmed by changes in shape of the correlation curve that were characteristic of unstable samples with polydisperse populations after heating at 40° C. (FIG. 8).

Figure 10:
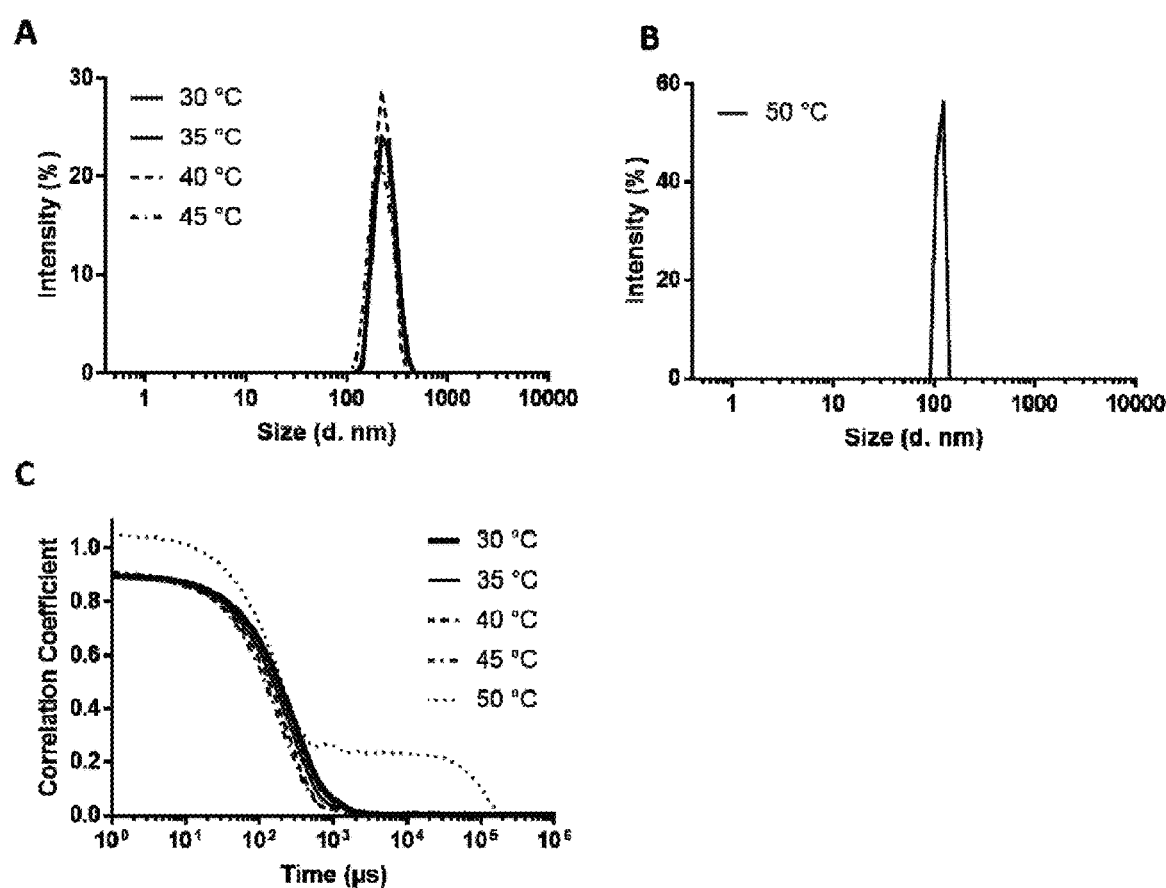
FIG. 10 shows (panels A-B) size distribution and (panel C) correlation curves of DFB NDs stabilized with F8H18 at temperatures ranging from 30 to 50° C.

Further experimental evidence for a direct effect of the FnHm co-surfactant on the PL shell of the DFB droplets emulsion is provided by observed significant increase of the NI) thermal stability. It was found that F8H18-stabilized NDs are stable up to 45° C. (FIGS. 10A and C), as this temperature increase did not induce any spontaneous vaporization of ND into MB. However, when the temperature reaches 50° C., which is well above the range of temperatures in the human body, most NDs vaporize to MBs (FIG. 10B) and the correlation curve showed the characteristic plateau (FIG. 10C). After reaching this temperature threshold, MBs were observed by naked eye in the DLS sample.

While non-stabilized NDs spontaneously vaporized at 40° C., NDs stabilized with a F8H18 cosurfactant were stable up to 45° C. These results demonstrate that the thermal stability of the DFB droplets can be tuned by modifying the properties of the nanodroplets shell with the inclusion of a diblock amphiphile co-surfactant.

Example 6

Figure 11:
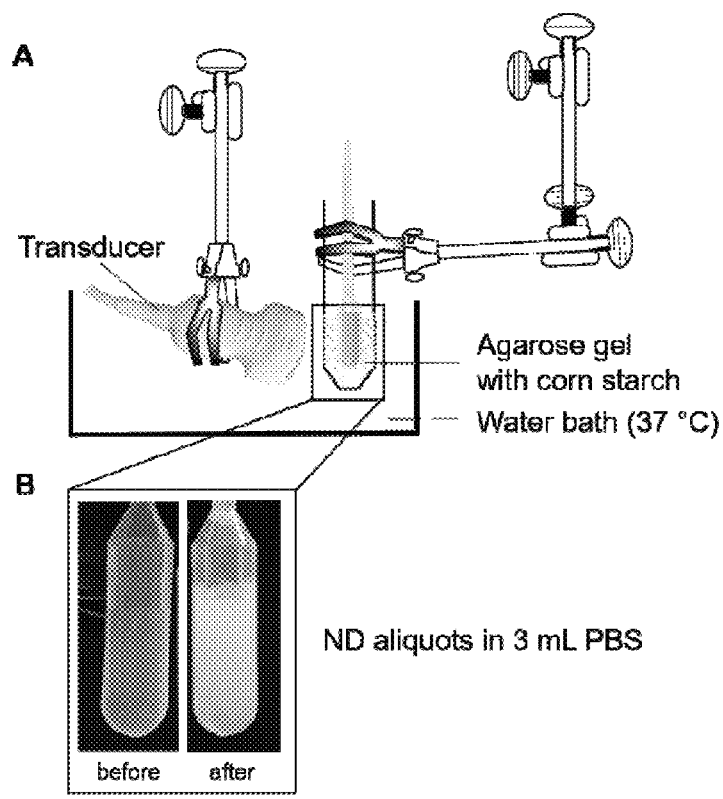
FIG. 11 shows (panel A) a schematic representation of an exemplary US vaporization setup, (panel B) a representative photograph of the transfer pipet bulb containing ND emulsions prior and post vaporization.
Figure 12:
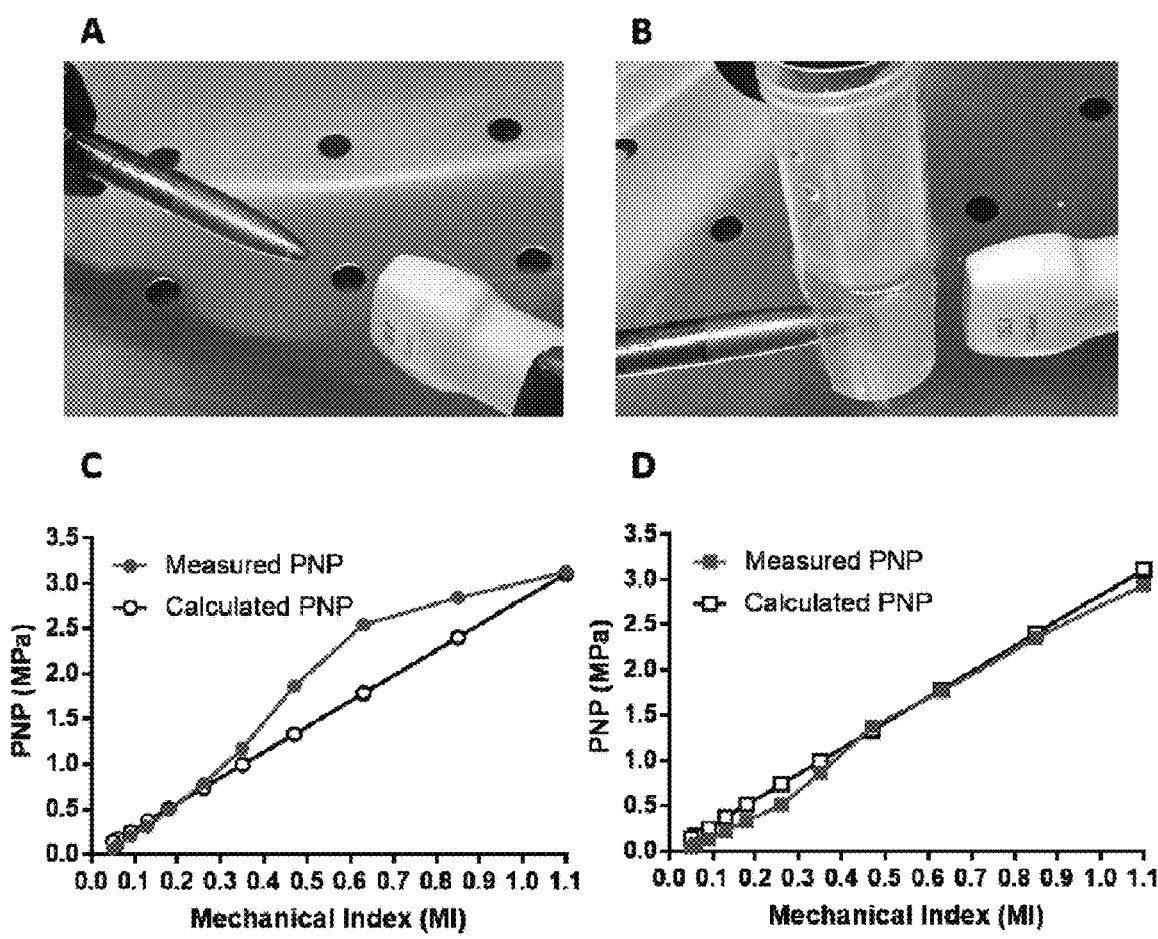
FIG. 12 shows calibration of peak negative pressure (PNP) output measurement by the clinical ultrasound machine used for vaporization experiments. (Panel A) A broadband hydrophone (Onda HGL-200) was oriented towards the Siemens 15L8 transducer, with tip and aperture of the hydrophone held at the electronic focus of the transducer, 2 cm away from the transducer face. (Panel B) To obtain recorded PNPs more accurately representing the experimental setup, agarose/cellulose and half of a pipette wall were placed in the path between the transducer and hydrophone. With settings identical to those used in the vaporization experiments, the maximal PNP amplitudes were recorded on an oscilloscope, with persistence recording mode used to find the largest amplitude peak at 10 different mechanical indices. PNPs recorded (panel C) using agarose/cellulose/pipette attenuation medium and (panel D) without attenuation medium, showing that attenuation medium resulted in recorded PNPs very similar to those calculated from on screen mechanical indices.

Ultrasound Triggered Phase Change of Non-Stabilized and Stabilized Decafluorobutane Nanodroplets ND emulsions with or without F8H18 were exposed to increasing acoustic output power on the clinical diagnostic ultrasound scanner Acuson Sequoia 512 to characterize droplet vaporization as a function of mechanical index (MI) at 37° C. FIG. 11 shows the schematic representation of the experimental setup. Droplet vaporization was achieved with transducer frequencies at 0.4 MI at 8 MHz and 1.4 MI at 2 MHz. Corresponding in situ peak negative pressure (PNP) output by the ultrasound transducer was measured using a calibrated hydrophone (FIG. 12)

Figure 13:
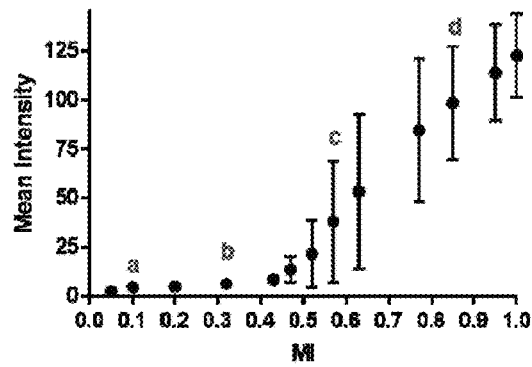
FIG. 13 shows contrast enhancement of DFB NDs (~1.6× $10^9$ NDs/mL) as a function of US input power for (panel A) non-stabilized NDs and (panel B) F8H18 stabilized NDs.
Figure 13:
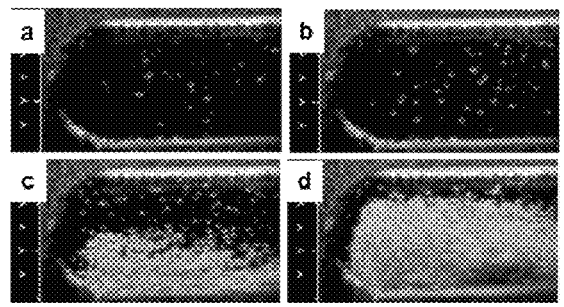
Figure 13:
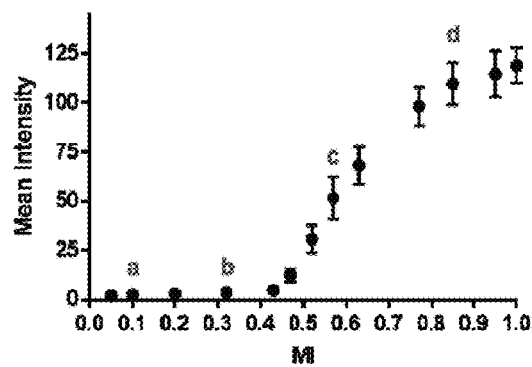
Figure 13:
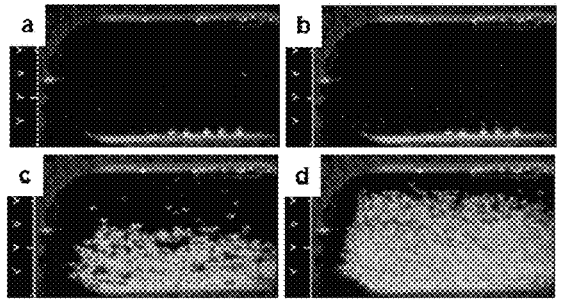
Figure 14:
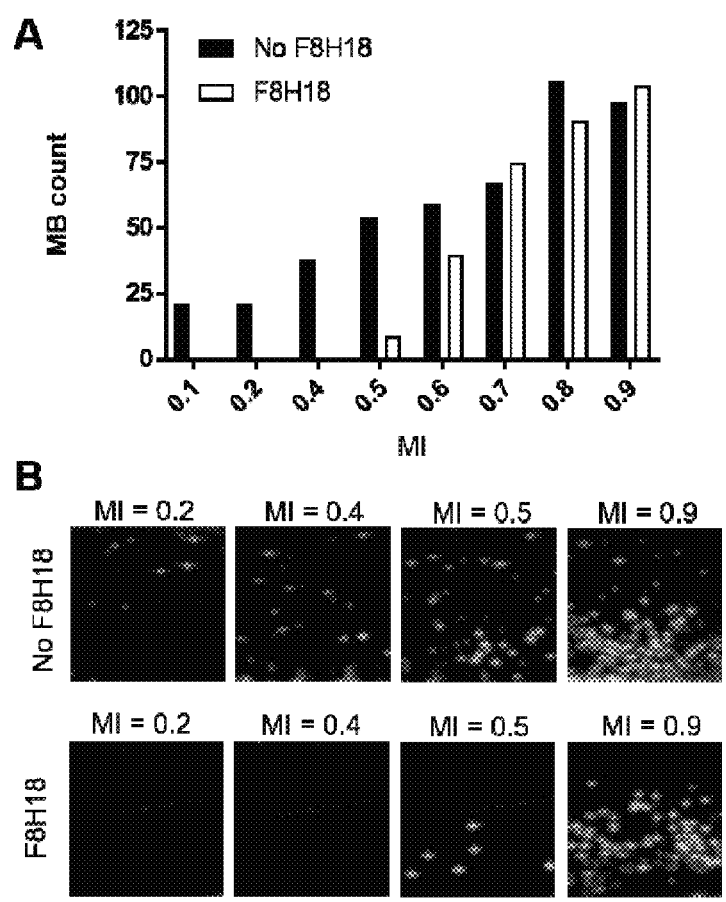
FIG. 14 shows the number of MBs created as a function of the US output power for non-stabilized. DFB NDs and F8H18 stabilized. DFB NDs (MB counted with ImageJ software, ~4×$10^8$ NDs/mL).

Both non-stabilized and stabilized NDs were stable at 37° C. (physiologic temperature) until exposed to ultrasound at moderate power, within the capabilities of diagnostic ultrasound machines (0.4 mechanical index or greater). DFB NDs underwent an ultrasound-triggered phase change at an in vivo compatible mechanical index (MI) of 0.5 at 37° C., as shown in FIGS. 13 and 14 (MI~0.5, 8 MHz, Siemens Acuson Sequoia C512).

A striking difference was observed at low MI (MI<0.45) between the two types of emulsions (~1.6×10$^9$ NDs/mL in both samples). In the case of non-stabilized NDs, few MBs were visible at low MI (FIG. 13A) MI=0.1 and b) MI=0.32), which is indicative of the vaporization of the liquid DEB core of some NDs without F8H18 into gas at the lowest tested US input power. In contrast, F8H18 stabilized emulsion showed no spontaneous phase transition to MBs until exposed to US at moderate power (≥0.45 MI) suggesting a prevention of phase transition at low US input power (FIG. 13B). To better quantify this stabilization from F8H18 co-surfactant, the number of MBs created was counted with ImageJ as a function of the US output power (FIG. 14). Altogether, these results proved that the introduction of F8H18 increases both the thermal and acoustic stability of the NDs.

Example 7

Figure 15:
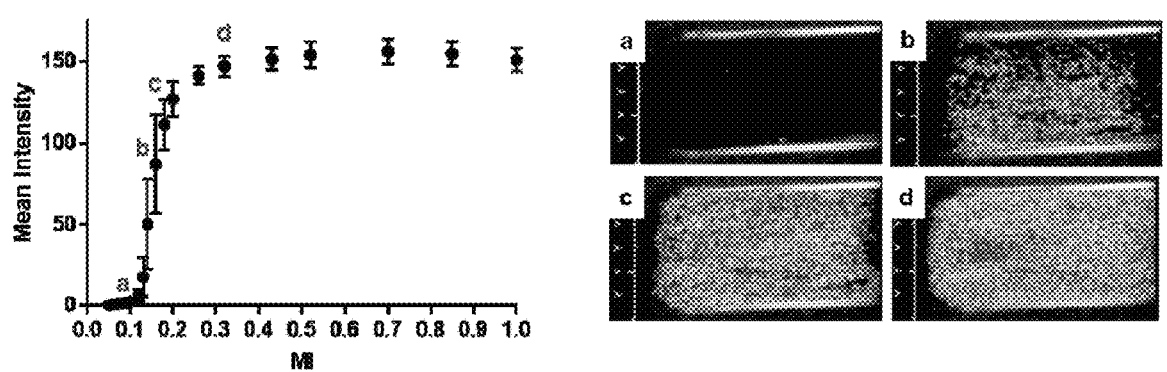
FIG. 15 shows contrast enhancement of OFP NDs (~4.5× $10^7$ NDs/mL) as a function of US input power.

Ultrasound Triggered Phase Change of Non-Stabilized Octafluoropropane Nanodroplets OFP NDs were stable at 37° C. (physiologic temperature) until exposed to ultrasound at low power (0.15 mechanical index or greater). NDs (~3.10$^7$ NDs/mL) underwent an ultrasound-triggered phase change at an in viva compatible mechanical index (MI) of 0.15 at 37° C., as shown in FIG. 15.

OFP ND emulsions were exposed to increasing acoustic output power on the clinical diagnostic ultrasound scanner Acuson Sequoia 512 to characterize droplet vaporization as a function of mechanical index (MI) at 37° C.

Example 8

Figure 16:
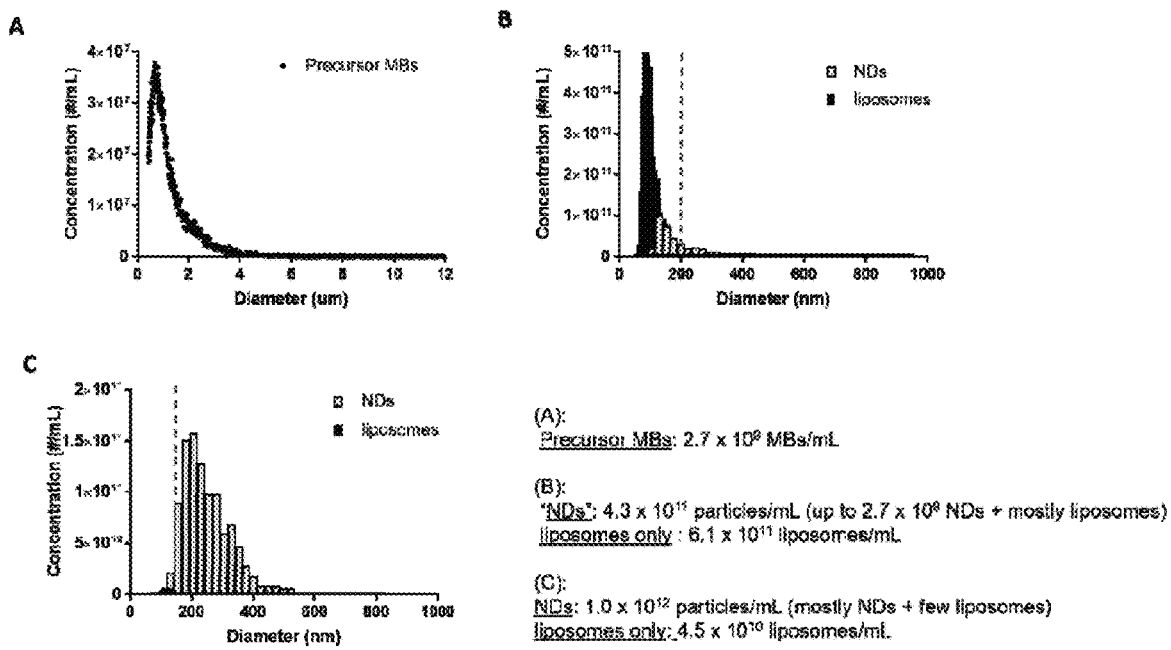
FIG. 16 shows a representative size distribution of precursor microbubbles measured by Multisizer (panel A), representative DFB ND emulsions and liposome size distributions measured by TRPS obtained by condensation (panel B) and our direct formulation (panel C). Particles with diameter on the left of the red bar are liposomes not NDs.
Figure 17:
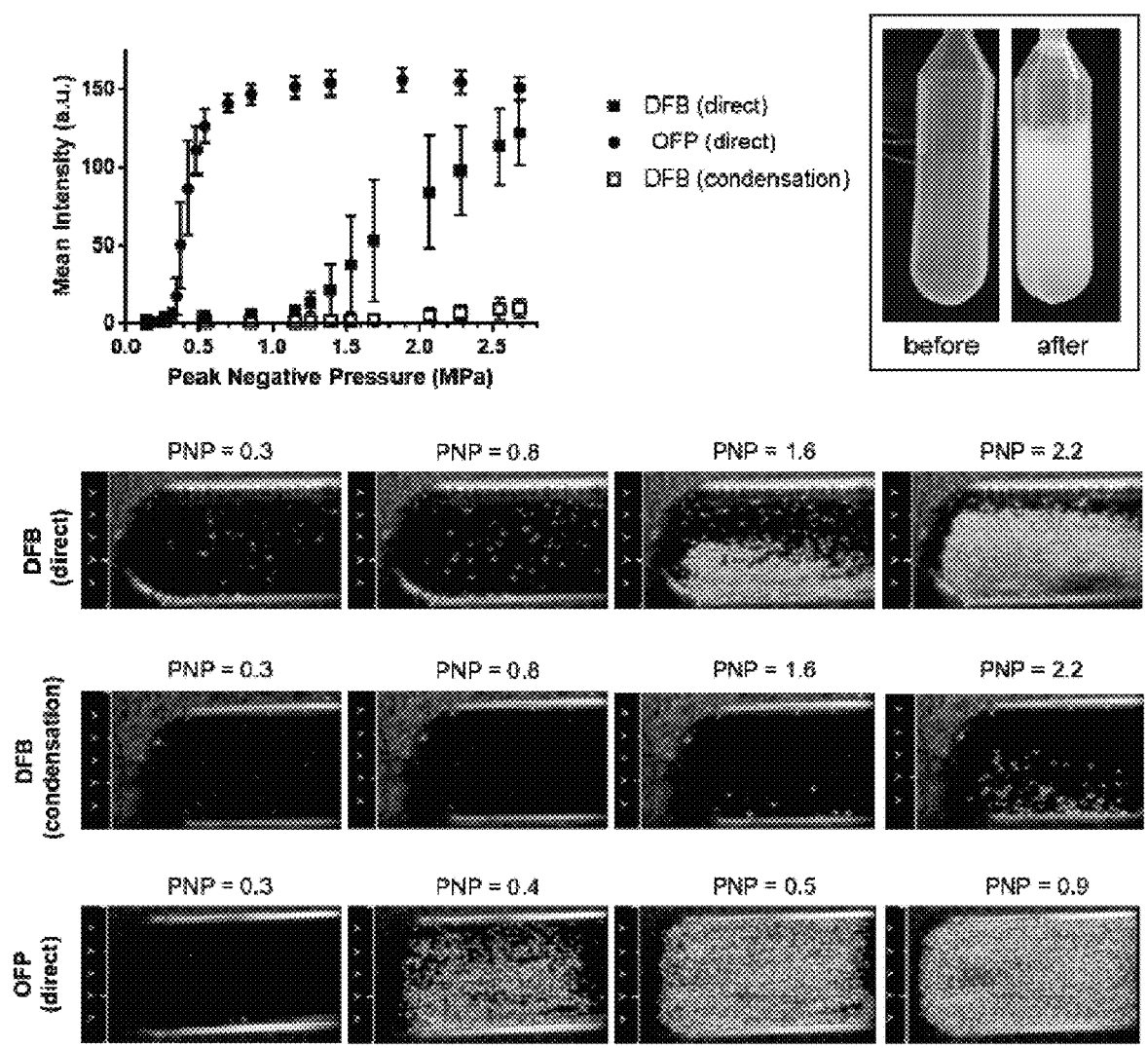
FIG. 17 shows contrast enhancement of 1.6×$10^9$ NDs/mL DFB and 4.5×$10^7$ NDs/mL OFP as a function of peak negative pressure (PNP). Representative US images and mean image intensity are shown as well as photographs of the transfer pipet bulb containing DEB NDs before and after US exposure (direct). Change in sample opacity is a hallmark feature of PCCA activation. "Direct" and "condensation" refer to the direct formulation of NDs by high pressure microfluidization and condensation of preformed MBs into NDs respectively.

Attributes of Non-Stabilized Decafluorobutane and Octafluoropropane Nanodroplets Produced Using Emulsification vs. Condensation DFB NDs prepared by condensation were prepared following the advocated reported procedure importantly, the same lipid composition, concentration and excipient as described in Example 1 were used to form precursor MBs (FIG. 16A-B). In parallel, liposomes obtained with both techniques were prepared and used as control experiment (FIG. 16B). To generate those liposomes, we used the same lipid composition and excipient and used both procedures without the addition of DFB (sonication and subsequent amalgamation or high pressure homogenizer). Using the currently advocated ND preparation technique through condensation of MBs, the concentration of ND samples is limited to the concentration of the precursor microbubbles (~10$^9$ MBs/mL). While it is well known that liposomes are generated during the production of MBs, there is no comprehensive report on their concentration. However, it is essential to evaluate the fraction of the population composed of liposomes post condensation, because those small size non echogenic liposomes will contribute to the count of sub-200 nm particles in the sample, which leads to overestimation of the ND concentration in the sample (FIG. 16B). Manufacturing DFB emulsions using the condensation method yielded a low concentration of NDs (up to 2.7×10$^9$ MBs/mL in 1 mL, FIG. 16A) in coexistence with a high number of liposomes. The concentration of small particles (ND+liposomes) obtained by condensation was measured at 4.3×10$^{11}$ particles/mL using TRPS (FIG. 16B). This concentration includes both NDs and liposomes with a maximal concentration of NDs of 2.7×10$^9$ NDs/mL (100% conversion of all MBs into NDs). As a control, liposomes obtained using the same technique in the absence of DFB and obtained a concentration of 6.1×10$^{11}$ liposomes/ML were formulated, which further demonstrates that in the absence of multiple washes to isolate MBs from liposomes, the majority of small particles present in the ND sample obtained by condensation is in fact liposomes. On the other hand, liposomes formulated by high pressure homogenization (FIG. 16C) are sub-150 nm and do not represent a significant portion in the NI) formulation. In average, a concentration of 10$^{12}$ NDs/mL was obtained for a final volume of 3 mL, using the method of the present invention. When OFP and DFB NDs were exposed to increasing acoustic power at 37° C., signal intensity remained at baseline without vaporization until the PNP passed 0.38 for OFP and 1.07 for DFB (FIG. 17, black spheres and black squares). Also note that while vaporization of DFB was gradual with increasing PNP, OFP signal reached a plateau at an PNP >0.8. As expected, these results confirm that PFC boiling point influences NDs vaporization threshold. NDs obtained by the condensation method only presented a low vaporization signal at an identical concentration (FIG. 17, white squares), which is in agreement with our hypothesis that the majority of small particles present in the ND sample is non echogenic liposomes and not NDs.

Example 9

Figure 18:
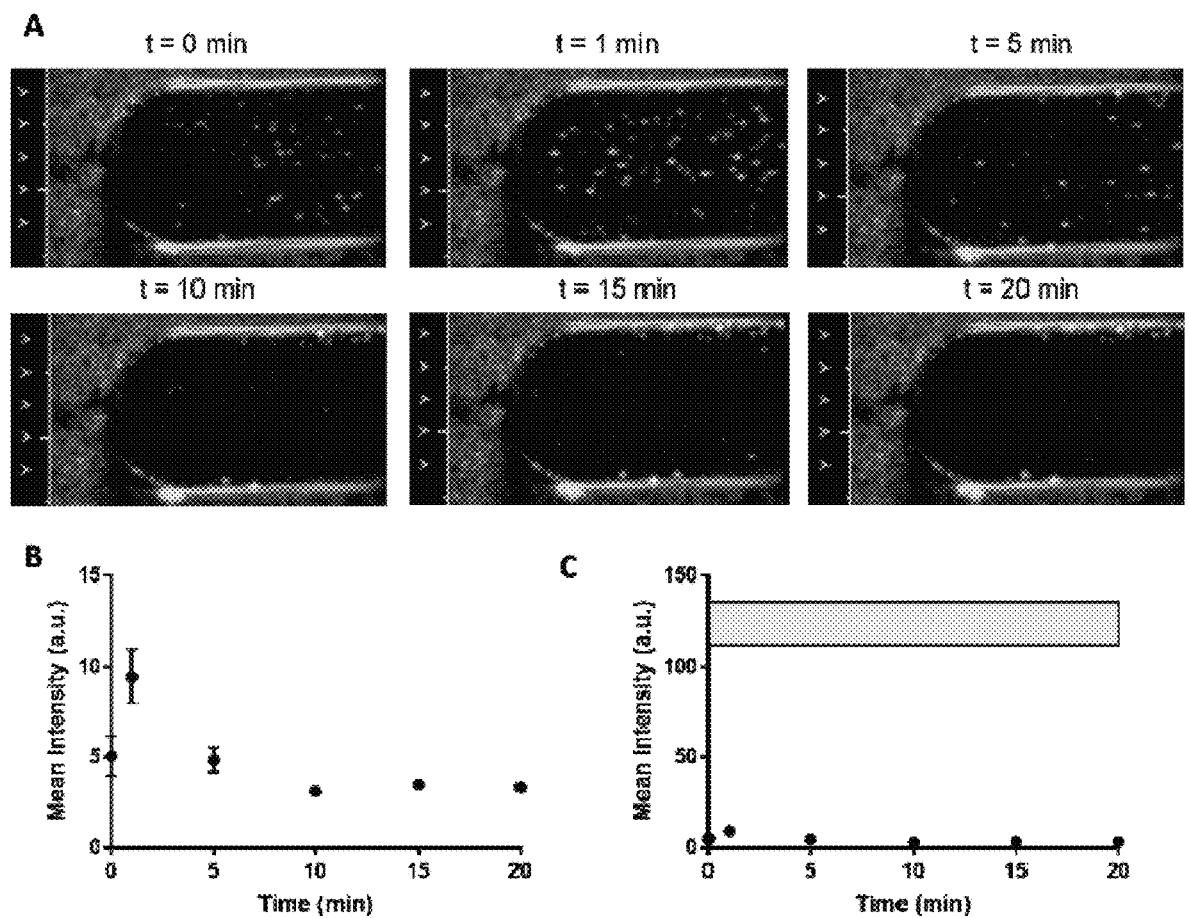
FIG. 18 shows a contrast enhancement of 1.6×$10^9$ NDs/ mL DFB as a function of incubation time at 37° C. at a sub-threshold insonation (MI–0.32, PNP=0.86). Representative US images (panel A) and mean image intensity (panels B and C) are shown. Grey bar in panel C represent the mean image intensity range above vaporization threshold at this concentration.

Thermal Stability of Non-Stabilized Decafluorobutane Nanodroplets at a Sub-Threshold Insonation Pressure Non-stabilized DFB NDs were monitored for microbubble formation due to thermal instability (i.e., spontaneous vaporization) over 20 minutes at 37° C., using B-mode, (FIG. 18). An experimental setup identical as shown in FIG. 11 was employed, but at an in situ peak negative pressure (PNP) of 0.86 (sub-threshold acoustic power) and with the same ND concentration used in the acoustic droplet vaporization evaluation (FIG. 13). When DFB NDs were exposed to a sub threshold acoustic power (onscreen MI=0.32, measured PNP=0.86) at 37° C., signal intensity remained at baseline without significant vaporization. As expected, only a very limited B-mode signal was observed during 20 minutes of incubation at 37° C. (mean intensity <10 a.u. vs ~125 a.u. for PNP at 2.68). This low signal was attributed to the small population of the largest droplets in the sample (the right-weighted tail in the distribution), less stable due to their lower Laplace pressure. B-mode is extremely sensitive and can detect a single microbubble. The lack of microbubble formation on B-mode over 20 minutes at 37° C. with a sub-threshold MI confirmed the thermal stability observed with DLS and TRPS.

Example 10

Figure 19:
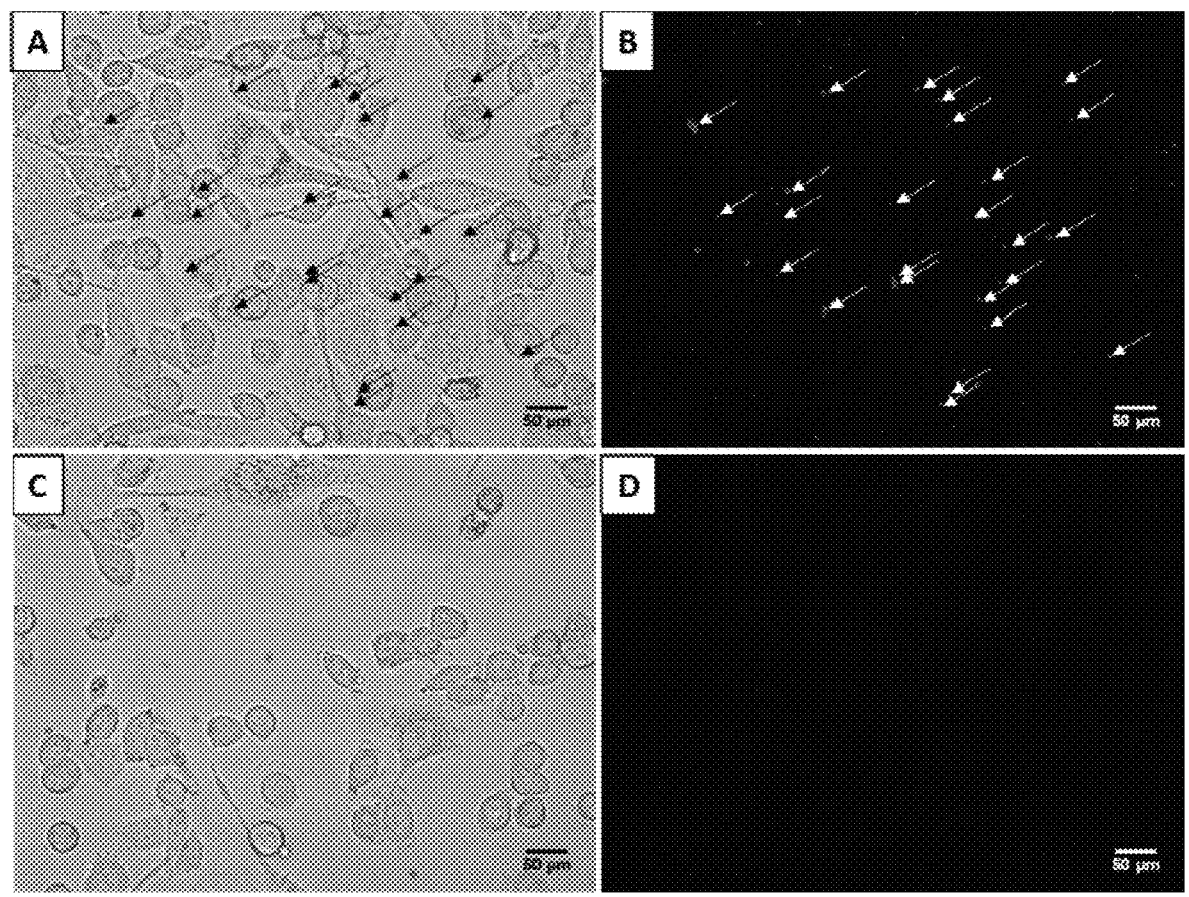
FIG. 19 shows DiD-labeled targeted DFB NDs (panels A and B) remained attached after washing but not control DiD-labeled NDs (panels C and D). Arrows pointing to DiD visible NDs in panel B are co-registered on the brightfield micrograph panel A. Panels A and C are representative brightfield microscopy images. Panels B and D are representative fluorescence microscopy images.

Preparation of DiD-Labeled EpCAM-Targeted Non-Stabilized Decafluorobutane Nanodroplets, Purification and In Vitro Cell Targeting DiD-labeled non-stabilized DEB NDs were prepared by first mixing DSPC, DSPE-PEG2000, 1,2-distearoyl-sn-glycero-3-phosphoethanolamine-N-[maleimide(polyethylene glycol)-5000] (DSPE-PEG5000Mal) in a molar ratio of 9:0.8:0.2. 8 µL of a 1 mM DiD solution in ethanol was then added once the lipid suspension was clear, followed by two more min of sonication at 68° C. The emulsion was then made using the same procedure as described above. Using the technique described by GX Shi et al., anti-Fc IgG was thiolated using Traut reagent and purified through a Zeba Spin Desalting column. Each antibody had approximately 3 thiol groups as measured with Measure-iT™ Thiol Assay Kit. One molar equivalent of thiolated anti EpCAM antibody or non-specific IgG as control, were added to 5×10 maleimide-terminated NDs and the mixture rotated for 1 h at room temperature on a rotating plate at 11 rpm. NDs were then washed twice by centrifugation (400 g, 25 min, 4° C.), incubated with one molar equivalent of anti-human CD326 antibody and washed again to remove excess antibodies. SK-BR-3 cells (5×105) were plated in a cell culture chamber slide (Millicell EZ SLIDES, Millipore, Billerica, Mass.) and 0.5 mL of McCoy's 5a medium added. Once cells were adherent, an excess of anti-human EpCAM labeled or control NDs ($1\times10^9$) was added and allowed to incubate at room temperature for 30 min. Cells were then washed 3 times with PBS to remove unbound NDs prior to microscopy (FIG. 19). A key advantage of ND formulations is their greater opportunity to target receptors in vivo compared to MBs because of their smaller size, larger particle count and longer circulation time. The challenge of producing targeted ND of low boiling point PFCs, is the additional time and manipulation required to attach and then wash excess ligands. Anti-EpCAM or non-specific IgG antibodies were attached to DiD-labeled DFB NDs and it was shown by fluorescence microscopy that targeted but not control NDs bound to EpCAM positive SK-BR-3 cells (FIG. 19).

An ideal PCCA formulation should produce NDs with a vaporization threshold achievable by diagnostic clinical ultrasound systems combined with an optimal thermal stability at room and physiological temperatures to allow for practical handling and performance. The formulation and emulsification technique presented here resulted in several unique properties to achieve this goal including: 1) sub-300 nm DFB NDs with narrow size distribution (PDI <0.2); 2) absence of MBs; 3) high ND concentration (>1012 NDs/mL); 4) high stability over 3 weeks at 4° C., and over 27 h at room temperature; and more importantly, over 2 h at physiological temperature (37° C.). In contrast, DFB NDs made with the condensation method were reported to be unstable at 4° C. after 5 h. Further, the condensation method resulted in droplets with a broad particle size distribution, and low particle concentration.

Another important distinction is that neither DFB nor OFP NDs vaporized at physiological temperature until they were exposed to ultrasound at clinically relevant power (≥0.4 MI for DFB, and ≥0.14 MI for OFP). As expected, when the NDs phase transitioned to MBs they produced a high contrast-to-noise ratio on B-mode US imaging.

In one embodiment, an element of the direct emulsification technique is that the resultant NDs are stable to allow further processing to produce labeled and functionalized systems, allowing the removal of non-PFC containing liposomes as well as unbound small molecules or antibodies. This purification capability assures optimal purity and paves the way for use of targeted NDs for molecular US-based theranostics. The in vitro results confirmed that NDs produced by direct emulsification and subsequent functionalization are able to target their intended receptors.

This invention confirms that direct emulsification of low boiling point PFC into liquid nanodroplets for phase-shift ultrasound controlled vaporization is possible. Emulsions of DFB were stable for >18 days (entire observation periods) at 4° C. and >1 day at room temperature allowing further processing for functionalization and purification. More important, DFB formulations were stable for at least 2 h at physiologic temperature without spontaneous vaporization, allowing ample time for targeting and tissue accumulation. They transitioned into MBs in vitro only when exposed to ultrasound at low PNP (0.38 for OFP and 1.07 for DFB) producing marked enhancement on B-mode US imaging.

While the present invention has been disclosed with reference to certain embodiments, it will be apparent that modifications and variations are possible without departing from the spirit and scope of the present invention as disclosed herein and as provided by the appended claims. Furthermore, it should be appreciated that all examples in the present disclosure, while illustrating embodiments of the invention, are provided as non-limiting examples and are, therefore, not to be taken as limiting the various aspects so illustrated. The present invention is intended to have the full scope defined by the present disclosure, the language of the following claims, and any equivalents thereof. Accordingly, the drawings and detailed description are to be regarded as illustrative and not as restrictive.

What is claimed is:

1. A method of producing a liquid perfluorocarbon (PFC) nanodroplet composition, comprising the steps of:
   combining a PFC liquid with a surfactant and co-surfactant to produce a fluid composition; and
   emulsifying said PFC liquid with said surfactant and said co-surfactant within said fluid composition through direct microfluidization at a pressure of at least 3,000 psi to reduce the size of PFC droplets within said fluid composition to form a nanodroplet composition having an average particle diameter of less than 300 nm,
   wherein said PFC has a boiling point of less than about 0° C.,
   wherein said surfactant comprises an amphiphilic phospholipid based compound,
   wherein said cosurfactant comprises a semifluorinated alkane, and
   wherein said emulsifying is performed at a temperature below 0° C.

2. The method of claim 1, wherein said semifluorinated alkane has a formula of $C_nF_{2n+1}C_mH_{2m+1}$.

3. The method of claim 1, wherein said PFC is decafluorobutane.

4. The method of claim 3, wherein said emulsifying is carried out at less than about −15° C.

5. The method of claim 1, wherein the concentration of said surfactant in the composition is no greater than about 3.5 mg/mL.

6. The method of claim 5, wherein the amount of said co-surfactant in the composition is about equimolar to the amount of said surfactant in the composition.

7. The method of claim 1, wherein said emulsifying is carried out at a pressure less than 23,000 psi.

8. The method of claim 7, wherein said emulsifying is carried out at a pressure no greater than about 13,000 psi.

9. The method of claim 7, wherein said emulsifying is carried out at a pressure of about 13,000 psi.

10. The method of claim 8, wherein said emulsifying is carried out at a pressure of at least about 8,000 psi.

11. The method of claim 1, wherein the nanodroplet composition having an average particle diameter of less than 300 nm is substantially free of microbubbles at −4° C. for at least 18 days.

12. The method of claim 1, wherein the nanodroplet composition having an average particle diameter of less than 300 nm is substantially free of microbubbles at 22° C. for at least one day.

13. The method of claim 1, wherein the nanodroplet composition having an average particle diameter of less than 300 nm is substantially free of microbubbles upon heating to physiological temperature.

14. The method of claim 13, wherein the nanodroplet composition having an average particle diameter of less than 300 nm is substantially free of microbubbles at physiological temperature for at least 2 hours.

15. The method of claim 1, wherein the nanodroplet composition having an average particle diameter of less than 300 nm is substantially free of microbubbles upon heating to 40° C.

16. The method of claim 1, wherein the nanodroplet composition having an average particle diameter of less than 300 nm is substantially free of microbubbles upon heating to 45° C.

17. The method of claim 1, wherein the nanodroplet composition has a concentration of at least $10^{11}$ nanodroplets/mL.

18. The method of claim 1, wherein said PFC is octafluoropropane.

19. The method of claim 18, wherein said emulsifying is carried out at less than about −35° C.

* * * * *

UNITED STATES PATENT AND TRADEMARK OFFICE
CERTIFICATE OF CORRECTION

| | |
|---|---|
| PATENT NO. | : 11,406,722 B2 |
| APPLICATION NO. | : 15/923845 |
| DATED | : August 9, 2022 |
| INVENTOR(S) | : Caroline de Gracia Lux et al. |

It is certified that error appears in the above-identified patent and that said Letters Patent is hereby corrected as shown below:

On the Title Page

Column 1, at item (12), "Lux et al." should be changed to --de Gracia Lux et al.--

In the Claims

Claim 11, Column 20, Line 9, the text "300 nm is substantially free of microbubbles at -4°C. for at" should be changed to --300 nm is substantially free of microbubbles at 4°C. for at--

Signed and Sealed this
Twenty-third Day of May, 2023

Katherine Kelly Vidal
*Director of the United States Patent and Trademark Office*